(12) United States Patent
Micallef

(10) Patent No.: US 10,184,945 B2
(45) Date of Patent: *Jan. 22, 2019

(54) METHOD FOR DETECTING NUCLEOSOMES CONTAINING HISTONE VARIANTS

(71) Applicant: BELGIAN VOLITION SPRL, Isnes (BE)

(72) Inventor: Jacob Vincent Micallef, London (GB)

(73) Assignee: BELGIAN VOLITION SPRL, Isnes (BE)

( * ) Notice: Subject to any disclaimer, the term of this patent is extended or adjusted under 35 U.S.C. 154(b) by 98 days.

This patent is subject to a terminal disclaimer.

(21) Appl. No.: 15/189,977

(22) Filed: Jun. 22, 2016

(65) Prior Publication Data

US 2016/0299152 A1 Oct. 13, 2016

Related U.S. Application Data

(62) Division of application No. 14/239,779, filed as application No. PCT/GB2012/052131 on Aug. 31, 2012, now Pat. No. 9,400,276.

(60) Provisional application No. 61/530,304, filed on Sep. 1, 2011.

(30) Foreign Application Priority Data

Sep. 1, 2011 (GB) .................................. 1115098.4

(51) Int. Cl.
*G01N 33/53* (2006.01)
*G01N 33/68* (2006.01)
*G01N 33/574* (2006.01)

(52) U.S. Cl.
CPC ..... *G01N 33/6875* (2013.01); *G01N 33/5308* (2013.01); *G01N 33/574* (2013.01); *G01N 33/57488* (2013.01); *G01N 33/6893* (2013.01); *G01N 2800/065* (2013.01); *G01N 2800/102* (2013.01); *G01N 2800/104* (2013.01); *G01N 2800/122* (2013.01); *G01N 2800/325* (2013.01); *G01N 2800/52* (2013.01)

(58) Field of Classification Search
None
See application file for complete search history.

(56) References Cited

U.S. PATENT DOCUMENTS

| 9,400,276 B2 | 7/2016 | Micallef |
| 2005/0069931 A1 | 3/2005 | Allis et al. |
| 2005/0233322 A1 | 10/2005 | Suer et al. |

FOREIGN PATENT DOCUMENTS

| EP | 2 270 510 | 1/2011 |
| WO | WO-02/076377 | 10/2002 |
| WO | WO-03/004050 | 1/2003 |
| WO | WO-03/070894 | 8/2003 |
| WO | WO-2005/019826 | 3/2005 |
| WO | WO-2005/040814 | 5/2005 |
| WO | WO-2007/017065 | 2/2007 |
| WO | WO-2011/000573 | 1/2011 |

OTHER PUBLICATIONS

Active Motif, The Newsletter of, Mar. 2011, 12(1):1-12.
Ausio et al., "Histone variants and histone modifications: a structural perspective", Biochem Cell Biol., 2001, 79(6):693-708.
Belyaev et al., "Differential underacetylation of histones H2A, H3 and H4 on the inactive X chromosome in human female cells", Human Genetics, 1996, 97:573-578.
Gamble et al., "This histone variant macroH2A1 marks repressed autosomal chromatin, but protects a subset of its target genes from silencing", Genes & Development, 2010, 24:21-32.
Hashizume et al., "Histone Methyltransferase PR-Set7 and Histone Variant H2A.Z, Induced during Hepatocarcinogenesis, Repress the Promoter Activity of the Tumor Marker Gene and the Ras-Induced Colony Formation Activity", J Health Sci, 2011, 57(3):264-273.
Hua et al., "Genomic analysis of estrogen cascade reveals histone variant H2A.Z associated with breast cancer progression", Mol Systems Bio, 2008, 4(188):1-14.
PathScan Pan-Methyl-Histone H3 (Lys9) Sandwich ELISA Kit, Cell Signaling Technology, 2012, 1-3.
Salgame et al., "An ELISA for detection of apoptosis", Nucleic Acids Research, 1997, 25(3):680-681.
Sporn et al., "Histone macroH2A isoforms predict the risk of lung cancer recurrence", Oncogene, 2009, 28:3423-3428.
White et al., "Preparation of the Site-Specific Antibodies to Acetylated Histones", Methods, 1999, 19:417-424.
Zeerleder et al., "Elevated nucleosome levels in systemic inflammation and sepsis", Critical Care Medicine, 2003, 31(7):1947-1951.
Holdenrieder et al., "Nucleosomes in Serum as a Marker for Cell Death", Clin. Chem. Lab. Med., 2001, 39(7): 596-605.
Williams et al., "Detection of Nucleosome Particles in Serum and Plasma From Patients With Systemic Lupus Erythematosus Using Monoclonal Antibody 4H7", J. Rheumatol., 2001, 28: 81-94.
Deligezer et al., "Sequence-Specific Histone Methylation is Detectable on Circulating Nucleosomes in Plasma", Molecular Diagnostics and Genetics, Apr. 15, 2008, Clinical Chemistry 54:7, pp. 1125-1131.

*Primary Examiner* — Changhwa J Cheu
(74) *Attorney, Agent, or Firm* — Foley & Lardner LLP

(57) ABSTRACT

The invention relates to a method for detecting and measuring the presence of mono-nucleosomes and oligo-nucleosomes and nucleosomes that contain particular histone variants and the use of such measurements for the detection and diagnosis of disease. The invention also relates to a method of identifying histone variant biomarkers for the detection and diagnosis of disease and to biomarkers identified by said method.

9 Claims, 14 Drawing Sheets

METHOD FOR DETECTING NUCLEOSOMES CONTAINING HISTONE VARIANTS

CROSS-REFERENCE TO RELATED APPLICATIONS

This application is a divisional application of U.S. application Ser. No. 14/239,779, filed on Mar. 27, 2014, which is a U.S. national stage application of International Patent Application No. PCT/GB2012/052131, filed on Aug. 31, 2012, which claims priority to GB Application No. 1115098.4, filed on Sep. 1, 2011, and U.S. Provisional Application No. 61/530,304, filed on Sep. 1, 2011, the content of each of these applications is incorporated herein in its entirety by reference.

FIELD OF THE INVENTION

The invention relates to a method for detecting and measuring the presence of mono-nucleosomes and oligo-nucleosomes and nucleosomes that contain particular histone variants and the use of such measurements for the detection and diagnosis of disease. The invention also relates to a method of identifying histone variant biomarkers for the detection and diagnosis of disease and to biomarkers identified by said method.

BACKGROUND OF THE INVENTION

The human body comprises several hundred cell types. All of these cell types contain the same genome but have widely different phenotypes and different functions in the body. This phenotypic diversity is due to the differential expression of the genome in different cell types. The control of differential gene expression is not entirely understood but the basic mechanisms include gene regulation by a number of interconnected epigenetic signals associated with the gene, including control of the chromatin packing as euchromatin or heterochromatin, control of nucleosome positioning and nuclease accessible sites, methylation of DNA and variation in the structure of the nucleosomes around which the DNA is wrapped.

The nucleosome is the basic unit of chromatin structure and consists of a protein complex of eight highly conserved core histones (comprising a pair of each of the histones H2A, H2B, H3, and H4). Around this complex are wrapped approximately 146 base pairs of DNA. Another histone, H1 or H5, acts as a linker and is involved in chromatin compaction. The DNA is wound around consecutive nucleosomes in a structure often said to resemble "beads on a string" and this forms the basic structure of open or euchromatin. In compacted or heterochromatin this string is coiled and super coiled into a closed and complex structure (Herranz and Esteller, 2007).

The structure of nucleosomes can vary by Post Transcriptional Modification (PTM) of histone proteins and by the inclusion of variant histone proteins. PTM of histone proteins typically occurs on the tails of the core histones and common modifications include acetylation, methylation or ubiquitination of lysine residues as well as methylation of arginine residues and phosphorylation of serine residues and many others. Histone modifications are known to be involved in epigenetic regulation of gene expression (Herranz and Esteller, 2007). The structure of the nucleosome can also vary by the inclusion of alternative histone isoforms or variants which are different gene or splice products and have different amino acid sequences. Histone variants can be classed into a number of families which are subdivided into individual types. The nucleotide sequences of a large number of histone variants are known and publicly available for example in the National Human Genome Research Institute NHGRI Histone DataBase (Mariño-Ramirez, L., Levine, K. M., Morales, M., Zhang, S., Moreland, R. T., Baxevanis, A. D., and Landsman, D. The Histone Database: an integrated resource for histones and histone fold-containing proteins. Database Vol. 2011. (Submitted) and http://genome.nhgri.nih.gov/histones/complete.shtml), the GenBank (NIH genetic sequence) DataBase, the EMBL Nucleotide Sequence Database and the DNA Data Bank of Japan (DDBJ).

Normal cell turnover in adult humans involves the creation by cell division of some $10^{11}$ cells daily and the death of a similar number, mainly by apoptosis. During the process of apoptosis chromatin is broken down into mononucleosomes and oligonucleosomes which are released from the cells. Under normal conditions the level of circulating nucleosomes found in healthy subjects is reported to be low. Elevated levels are found in subjects with a variety of conditions including many cancers, auto-immune diseases, inflammatory conditions, stroke and myocardial infarction (Holdenreider & Stieber, 2009).

Mononucleosomes and oligonucleosomes can be detected by Enzyme-Linked ImmunoSorbant Assay (ELISA) and several methods have been reported (Salgame et al, 1997; Holdenrieder et al, 2001; van Nieuwenhuijze et al, 2003). These assays typically employ an anti-histone antibody (for example anti-H2B, anti-H3 or anti-H1, H2A, H2B, H3 and H4) as capture antibody and an anti-DNA or anti-H2A-H2B-DNA complex antibody as detection antibody. Using these assays workers in the field report that the level of nucleosomes in serum is higher (by up to an order of magnitude) than in plasma samples taken from the same patients. This is also true for serum and plasma measurements of DNA made by PCR (Holdenrieder et al, 2005). The reason for this is not known but the authors speculate that it may be due to additional release of DNA during the clotting process. However, we have found that the results of nucleosome ELISA assays of the current art do not agree with each other. Furthermore, although most circulating DNA in serum or plasma is reported to exist as mono-nucleosomes and oligo-nucleosomes (Holdenrieder et al, 2001), measured levels of nucleosomes and DNA in serum or plasma do not agree well. The correlation coefficient between ELISA results for circulating cell free nucleosomes levels and circulating DNA levels as measured by real time PCR (Polymerase Chain Reaction) has been reported to be $r=0.531$ in serum and $r=0.350$ in plasma (Holdenrieder et al, 2005).

Current nucleosome ELISA methods are used in cell culture, primarily as a method to detect apoptosis (Salgame et al, 1997; Holdenrieder et al, 2001; van Nieuwenhuijze et al, 2003), and are also used for the measurement of circulating cell free nucleosomes in serum and plasma (Holdenrieder et al, 2001). Cell free serum and plasma nucleosome levels released into the circulation by dying cells have been measured by ELISA methods in studies of a number of different cancers to evaluate their use as a potential biomarker (Holdenrieder et al, 2001). Mean circulating nucleosome levels are reported to be high in most, but not all, cancers studied. The highest circulating nucleosome levels were observed in lung cancer subjects. The lowest levels were observed in prostate cancer, which were within the normal range of healthy subjects. However, patients with malignant tumours are reported to have serum nucleosome concentrations that varied considerably and some patients with advanced tumour disease were found to have low circulating nucleosome levels, within the range measured for healthy subjects (Holdenrieder et al, 2001). Because of this and the variety of non-cancer causes of raised nucleosome levels, circulating nucleosome levels are not used clinically as a biomarker of cancer (Holdenrieder and Stieber, 2009). Surprisingly we have shown that many cancer subjects whose circulating nucleosome levels are low or undetectable as measured by these nucleosome ELISA methods of the current art, do in fact have raised levels of circulating cell free nucleosomes. We have designed and demonstrated novel ELISA methods for nucleosomes that detect nucleosomes not detected by ELISA methods of the current art.

ELISA methods for the detection of histone PTMs are also known in the art. ELISA methods for PTM detection in free histone proteins (not attached to other histones and DNA in a nucleosome complex) are used for the detection of PTMs in histones extracted, usually by acid extraction, from cell lysates. Immunoassay for the detection of PTMs in circulating cell free nucleosomes has been reported (Bawden et al, 2005). A method for ELISA detection of histone PTMs in purified nucleosomes directly coated to microtitre wells has recently been reported (Dai et al, 2011). In this method nucleosomes obtained by digestion of chromatin extracts from cultured cells are coated directly to microtitre wells and reacted with anti-PTM antibodies. It will be clear to those skilled in the art that this method requires relatively pure nucleosome samples and is not suitable for the direct measurement of histone PTMs in complex biological media such as blood or serum.

A modified chromatin immunoprecipitation (ChIP) method for the detection of a histone PTM (H3K9Me, histone H3 monomethylated at lysine residue K9) in cell free nucleosomes associated with a particular DNA sequence has been reported in plasma. The level of sequence specific histone methylation was reported to be independent of the concentration of circulating nucleosomes (Deligezer et al, 2008).

In addition to the epigenetic signaling mediated by nucleosome position and nucleosome structure (in terms of both constituent histone protein variant and PTM structures), control of gene expression in cells is also mediated by modifications to DNA nucleotides including the cytosine methylation status of DNA. It has been known in the art for some time that DNA may be methylated at the 5 position of cytosine nucleotides to form 5-methylcytosine. Methylated DNA in the form of 5-methylcytosine is reported to occur at positions in the DNA sequence where a cytosine nucleotide occurs next to a guanine nucleotide. These positions are termed "CpG" for shorthand. It is reported that more than 70% of CpG positions are methylated in vertebrates (Pennings et al, 2005). Regions of the genome that contain a high proportion of CpG sites are often termed "CpG islands", and approximately 60% of human gene promoter sequences are associated with such CpG islands (Rodriguez-Paredes and Estellar, 2011). In active genes these CpG islands are generally hypomethylated. Methylation of gene promoter sequences is associated with stable gene inactivation. DNA methylation also commonly occurs in repetitive elements including Alu repetitive elements and long interspersed nucleotide elements (Herranz and Estellar, 2007; Allen et al, 2004).

The involvement of DNA methylation in cancer was reported as early as 1983 (Feinberg and Vogelstein, 1983). DNA methylation patterns observed in cancer cells differ from those of healthy cells. Repetitive elements, particularly around pericentromeric areas, are reported to be hypomethylated in cancer relative to healthy cells but promoters of specific genes have been reported to be hypermethylated in cancer. The balance of these two effects is reported to result in global DNA hypomethylation in cancer cells (Rodriguez-Paredes; Estellar, 2007).

Hypermethylation of certain specific genes can be used as a diagnostic biomarker for cancers. For example a method reported for detection of hypermethylation of the Septin 9 gene by PCR amplification of DNA extracted from plasma was reported to detect 72% of colon cancers with a false positive rate of 10% (Grutzmann et al, 2008). The DNA methylation status of specific genes or loci is usually detected by selective bisulphite deamination of cytosine, but not 5-methylcytosine, to uracil, leading to a primary DNA sequence change that can be detected by sequencing or other means (Allen et al, 2004).

Global DNA hypomethylation is a hallmark of cancer cells (Estellar 2007 and Hervouet et al, 2010). Global DNA methylation can be studied in cells using immunohistochemistry (IHC) techniques. Alternatively the DNA is extracted from the cells for analysis. A number of methods have been reported for the detection of global methylation in DNA extracted from cells including restriction digestion and nearest-neighbour analysis, fluorescent assays using chloracetaldehyde, inverse determination by methylation of all CpG sites using DNA methyltransferase in conjunction with tritium-labelled S-adenosyl methionine to calculate the amount of unmethylated CpG and digestion of DNA into single nucleotides for analysis by high-performance liquid chromatography, thin-layer chromatography, or liquid chromatography followed by mass spectroscopy. The disadvantages of these methods are that they are labour intensive and/or require large amounts of good quality extracted DNA (Allen et al 2004). PCR based methods involving bisulfite deamination overcome the need for large amounts of DNA but must amplify specific genome regions, typically repetitive sequences, as indicative of the total genome content of 5-methylcytosine (Allen et al 2004). These methods for global DNA methylation measurement have been used to study DNA extracted from a variety of cells and tissues. Some workers have studied DNA extracted from white blood cells in whole blood as this is easier to obtain in a minimally-invasive manner (Moore et al, 2008; Ting Hsiung et al, 2007; Mansour et al, 2010). Liquid Chromatography with mass spectrometry is considered the gold standard for global DNA methylation measurement but it is costly, and the DNA must be digested to the single nucleotide level prior to analysis (Vasser et al, 2009).

Recent methods for the estimation of global DNA methylation include ultra high-pressure liquid chromatography with mass spectrometry of hydrolysed DNA extracted from tissue (Zhang et al, 2011) and a methylation-specific digital sequencing (MSDS) method (Ogoshi et al 2011). A classical competitive immunoassay for global DNA methylation (as well as a similar assay for global 5-hydroxymethylcytosine methylation) has been described. In this method DNA extracted from cells or tissues is added to a microtitre well coated with a 5-methylated cytidine conjugate, an anti-5-methylcytidine antibody is added and the distribution of antibody binding between the coated 5-methylcytidine conjugate and the methylated DNA in the extracted sample is compared to that of known standards to estimate the global DNA methylation level present in the sample (Cell Biolabs, 2011). In another immunoassay like method DNA extracted from tissues or from plasma or serum samples is coated to a microtitre well and methylated DNA is detected using an anti-5-methylcytosine antibody (Vasser, et al, 2009; Epigentek, 2009). A disadvantage of these methods is that they require extraction of DNA involving the denaturation and removal of all nucleosome and chromatin structure from the DNA. They are not suited for example; for the direct measurement of global DNA methylation in biological fluids such as tissue lysate, blood, plasma or serum without a DNA extraction step.

5-hydroxymethyl modification of cytosine bases in DNA has also been reported. The role of 5-hydroxymethylation is not yet well understood but it appears to be involved in gene regulation (Stroud et al, 2011).

Current methods for the detection of global DNA methylation involve extraction or purification of the DNA and are not suitable for rapid, high throughput, low cost, minimally-invasive diagnostic methods. Similarly, analysis of DNA for other modified or unusual bases (for example uracil, inosine, xanthine, and hypoxanthine) can only be investigated by the analysis of substantially pure or extracted DNA. Such analysis cannot be carried out directly in complex biological media such as tissue lysate, blood, plasma or serum.

Histone variants (also known as histone isoforms) are also known to be epigenetic regulators of gene expression (Herranz and Esteller, 2007). Histone variants have been studied in vivo and in vitro using a variety of techniques including knock-down studies of the gene encoding a particular variant (for example using RNAi knock-down), chromatin immunoprecipitation, stable isotope labeling of amino acids and quantitative mass spectrometry proteomics, immunohistochemistry and Western Blotting (Whittle et al, 2008; Boulard et al, 2010; Sporn et al, 2009; Kapoor et al, 2010; Zee et al, 2010; Hua et al, 2008).

Immunohistochemistry studies of histone variant expression in tissue samples removed at surgery or by biopsy from subjects diagnosed with lung cancer, breast cancer and melanoma have been reported. These immunohistochemistry studies report that staining of histone macroH2A (mH2A) and H2AZ variants in resected cancer tissue samples may have prognostic application in these cancers (Sporn et al, 2009, Hua et al, 2008, Kapoor et al, 2010). One disadvantage of immunohistochemical methods for clinical use is that tissue sample collection is invasive involving surgery or biopsy. Another disadvantage of immunohistochemistry methods is that they are unsuited for early diagnosis or for screening diagnostics as a reasonable expectation of the disease must usually already exist before a biopsy or tissue resection is made. Minimally invasive blood ELISA tests are suitable for a wider range of applications and would overcome these disadvantages and be preferable for the patient as well as faster, lower cost and more high-throughput for the healthcare provider.

However, cell free nucleosomes containing particular nucleotides, modified nucleotides or histone variants have not been measured in blood or any other medium and no such measurements have been suggested or contemplated. No studies on the presence or absence of nucleotides, modified nucleotides or histone variants in cell free nucleosomes in blood have been reported nor whether they have value as blood biomarkers of disease. There are currently no methods for the detection or measurement of nucleotides, modified nucleotides or histone variants in intact cell free nucleosomes. We now report methods for such tests and their use in plasma and serum samples taken from healthy and diseased subjects. Surprisingly we have shown that high levels of intact nucleosomes comprising specific histone variants can be detected in plasma and serum samples for which no nucleosomes, or low levels, are detected by nucleosome ELISA methods of the current art.

SUMMARY OF THE INVENTION

According to a first aspect of the invention there is provided a cell free nucleosome comprising a histone variant or histone isoform for use as a biomarker for the diagnosis of cancer, cardiomyopathy, systemic lupus erythematosus, colitis, chronic obstructive pulmonary disorder, Crohn's disease and rheumatoid arthritis.

According to a second aspect of the invention there is provided a method for detecting the presence of a nucleosome containing a histone variant or histone isoform in a sample which comprises the steps of:
(i) contacting the sample with a binding agent which binds to the histone variant or histone isoform;
(ii) detecting or quantifying the binding of said binding agent to the histone variant or histone isoform in the sample; and
(iii) using the presence or degree of such binding as a measure of the presence of nucleosomes containing the histone variant or histone isoform in the sample.

According to a third aspect of the invention there is provided a method for detecting the presence of a nucleosome containing a histone variant or histone isoform in a sample which comprises the steps of:
(i) contacting the sample with a first binding agent which binds to nucleosomes;
(ii) contacting the nucleosomes or sample with a second binding agent which binds to the histone variant or histone isoform;
(iii) detecting or quantifying the binding of said second binding agent to histone variant or histone isoform in the sample; and
(iv) using the presence or degree of such binding as a measure of the presence of nucleosomes containing the histone variant or histone isoform in the sample.

According to a fourth aspect of the invention there is provided a method for detecting the presence of a nucleosome containing a histone variant or histone isoform in a sample which comprises the steps of:
(i) contacting the sample with a first binding agent which binds to the histone variant or histone isoform;
(ii) contacting the nucleosomes or sample with a second binding agent which binds to nucleosomes;
(iii) detecting or quantifying the binding of said second binding agent to nucleosomes in the sample; and
(iv) using the presence or degree of such binding as a measure of the presence of nucleosomes containing the histone variant or histone isoform in the sample.

According to a further aspect of the invention there is provided a method for detecting the presence of a nucleosome containing a histone variant or histone isoform in a blood, serum or plasma sample which comprises the steps of:
(i) removing, releasing or extracting the histone variant or isoform from the nucleosome complex to produce a free histone variant or isoform moiety
(ii) detecting or quantifying the free histone variant or isoform in the sample; and
(iii) using the presence or amount of free histone variant or isoform as a measure of the presence of nucleosomes containing the histone variant or histone isoform in the sample.

According to a further aspect of the invention there is provided a method for detecting the presence of a nucleosome containing a histone variant or histone isoform in a cell which comprises the steps of:
(i) isolating chromatin from a cell;
(ii) digesting, sonicating or otherwise breaking down the chromatin to form mono-nucleosomes and/or oligo-nucleosomes; and
(iii) detecting or measuring the presence of the histone variant or histone isoform in the said nucleosomes according to a method of the invention.

According to a further aspect of the invention there is provided a method for detecting or diagnosing a disease status in an animal or a human subject which comprises the steps of:
(i) detecting or measuring nucleosomes containing a histone variant or histone isoform in a body fluid of a subject; and
(ii) using the nucleosome associated histone variant or histone isoform level detected to identify the disease status of the subject.

According to a further aspect of the invention there is provided a method for assessment of an animal or a human subject for suitability for a medical treatment which comprises the steps of:
(i) detecting or measuring nucleosomes containing a histone variant or histone isoform in a body fluid of the subject; and
(ii) using the nucleosome associated histone variant or histone isoform level detected as a parameter for selection of a suitable treatment for the subject.

According to a further aspect of the invention there is provided a method for monitoring a treatment of an animal or a human subject which comprises the steps of:
(i) detecting or measuring nucleosomes containing a histone variant or histone isoform in a body fluid of the subject;
(ii) repeating the detection or measurement of nucleosomes containing a histone variant or histone isoform in a body fluid of the subject on one or more occasions; and
(iii) using any changes in the nucleosome associated histone variant or histone isoform level detected as a parameter for any changes in the condition of the subject.

According to a further aspect of the invention there is provided a method for identifying a histone variant or histone isoform biomarker for detecting or diagnosing a disease status in an animal or a human subject which comprises the steps of:
(i) detecting or measuring nucleosomes containing the histone variant or histone isoform in a body fluid of the subject;
(ii) detecting or measuring nucleosomes containing the histone variant or histone isoform in a body fluid of a healthy subject or a control subject; and
(iii) using the difference between the levels detected in diseased and control subjects to identify whether a histone variant or histone isoform is useful as a biomarker for the disease status.

According to a further aspect of the invention there is provided a biomarker identified by said method of the invention.

According to a further aspect of the invention there is provided a kit for the detection of a nucleosome associated histone variant or histone isoform which comprises a ligand or binder specific for the histone variant or histone isoform or component part thereof, or a structural/shape mimic of the histone variant or histone isoform or component part thereof, together with instructions for use of the kit.

N1 Metastasis in ipsilateral peribronchial and/or ipsilateral hilar lymph nodes and intrapulmonary nodes, including involvement by direct extension N2 Metastasis in ipsilateral mediastinal and/or subcarinal lymph node(s)

N3 Metastasis in contralateral mediastinal, contralateral hilar, ipsilateral or contralateral scalene, or supraclavicular lymph node(s)

T1: tumor<3 cm
T2: 3 cm<tumor<7 cm
T3: tumor>7 cm
T4: tumor of any size that invades other organ, tissue
M0: no spread of disease beyond regional nymph nodes
M1: spread of disease to distant metastases.

Figure 23:
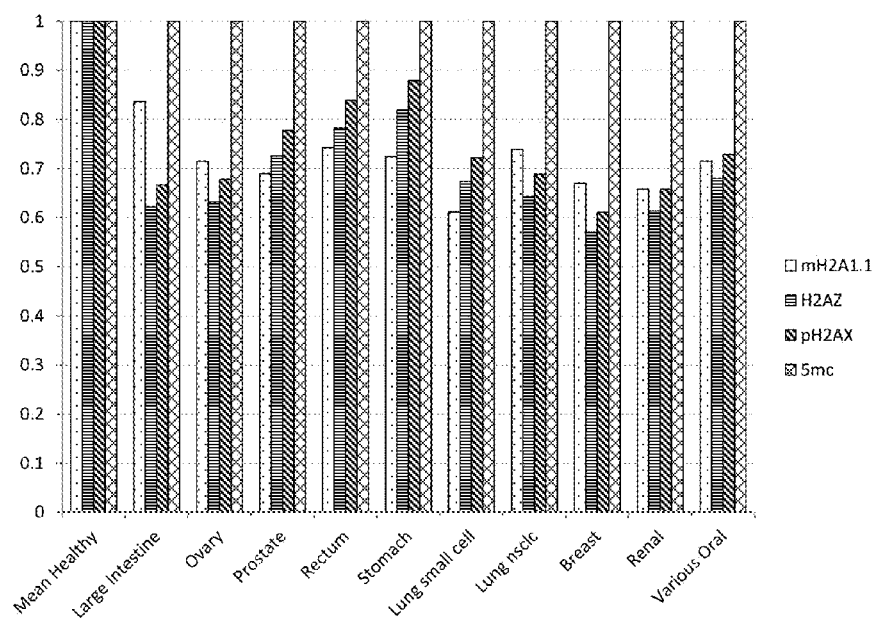

FIG. 23. Mean cell-free nucleosome associated levels of nucleotides and types of histones detected using ELISA methods of the invention for EDTA plasma samples taken from 10 different cancer diseases normalised as a proportion of nucleosome associated 5-methylcytosine (5mc) methylated DNA levels and expressed relative to the mean proportions found in 11 healthy subjects.

Figure 24:
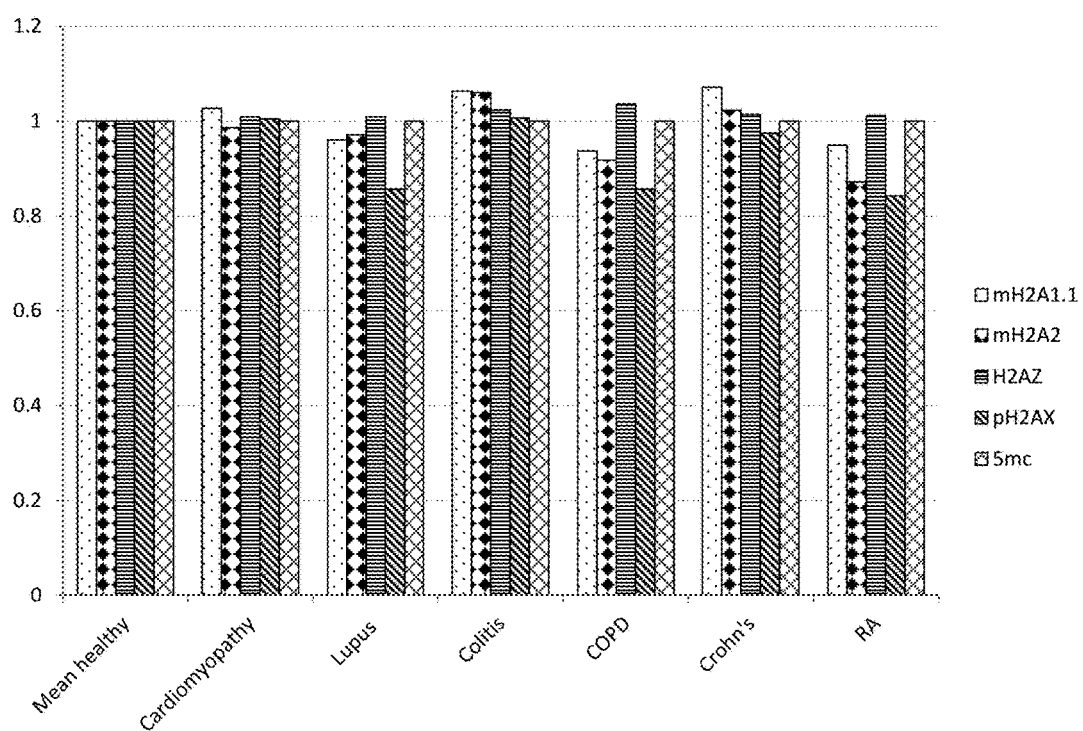

FIG. 24. Mean cell-free nucleosome associated levels of nucleotides and types of histones detected using ELISA methods of the invention for EDTA plasma samples taken from 2 cardiomyopathy patients, 10 systemic lupus erythematosus (lupus) patients, 12 ulcerative colitis patients, 10 chronic obstructive pulmonary disease (COPD) patients, 8 Crohn's disease patients and 10 rheumatoid arthritis (RA) patients normalised as a proportion of nucleosome associated 5-methylcytosine (5mc) methylated DNA levels and expressed relative to the mean proportions found in 11 healthy subjects.

DETAILED DESCRIPTION OF THE INVENTION

According to a first aspect of the invention there is provided a cell free nucleosome comprising a histone variant or histone isoform for use as a biomarker for the diagnosis of cancer, cardiomyopathy, systemic lupus erythematosus, colitis, chronic obstructive pulmonary disorder, Crohn's disease and rheumatoid arthritis.

In one embodiment, the nucleosome is a mononucleosome or oligonucleosome.

According to one particular aspect of the invention which may be mentioned, there is provided the use of a histone variant or histone isoform as a biomarker for the diagnosis of cancer.

In one embodiment, the cancer is a cancer of the bladder, breast, colon, cervix, esophagus, kidney, large intestine, lung, oral cavity, ovary, pancreas, prostate, rectum, skin or stomach. In one particular embodiment which may be mentioned, the cancer is a cancer of the colon, lung, oral cavity or pancreas.

We have developed ELISA tests for the detection and measurement of nucleosomes containing the histone variants macroH2A1.1 (mH2A1.1), macroH2A2 (mH2A2) and H2AZ. We have used an anti-histone antibody as capture antibody for these assays in combination with an appropriate specific anti-histone variant antibody as detection antibody. We have shown that these ELISA methods work with alternative anti-nucleosome capture antibodies. We have also used the assays to show that nucleosomes containing specific histone variants can be measured in blood samples taken from diseased subjects and are discriminating for use as non-invasive or minimally invasive biomarkers. The histone variant levels detected in nucleosomes in serum and plasma samples taken from diseased subjects, relative to levels of other nucleosome epitopes, differ from those detected in samples from healthy subjects. In addition the pattern of levels of nucleosomes containing different histone variants detected in nucleosomes in samples from different diseases was found to differ for different diseases, particularly when the nucleosome associated histone variant patterns were examined in combination with the patterns determined for nucleosomes containing different nucleotides and PTMs, such that a differential diagnosis of disease was possible. It will be clear to those skilled in the art that inclusion of tests for nucleosomes containing different or additional histone variants or histone modifications or nucleotides would be likely to improve the discrimination of differential diagnosis using such patterns.

Figure 4:
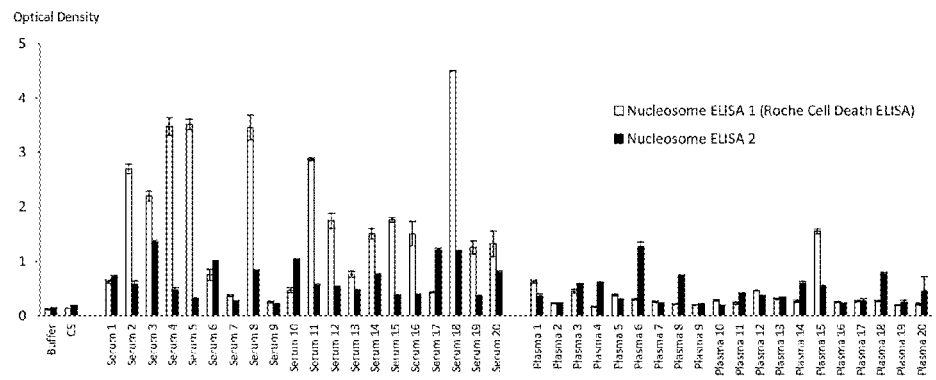
FIG. 4. Nucleosome levels detected for serum and EDTA plasma samples taken from 20 healthy volunteers using nucleosome ELISA methods of the current art.
Figure 5:
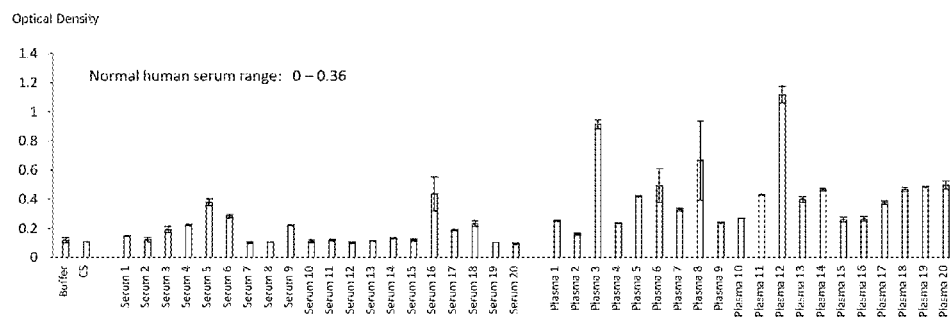
FIG. 5. Cell free nucleosome associated levels of histone variant mH2A1.1 detected for serum and EDTA plasma samples taken from 20 healthy volunteers using the ELISA of the invention.
Figure 6:
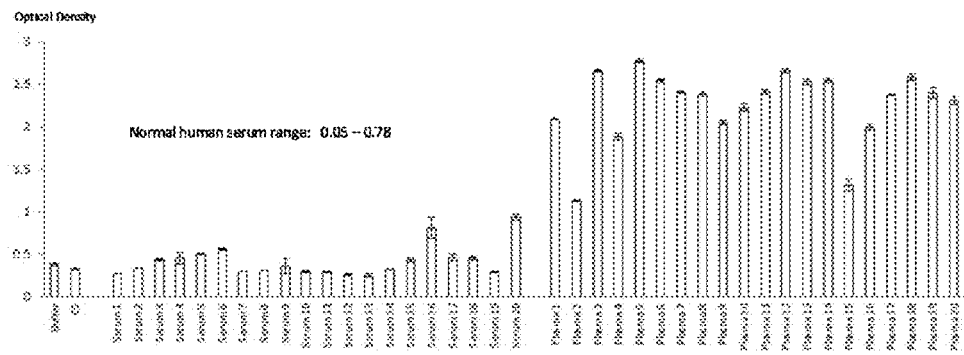
FIG. 6. Cell free nucleosome associated levels of histone variant mH2A2 detected for serum and EDTA plasma samples taken from 20 healthy volunteers using the ELISA of the invention.
Figure 7:
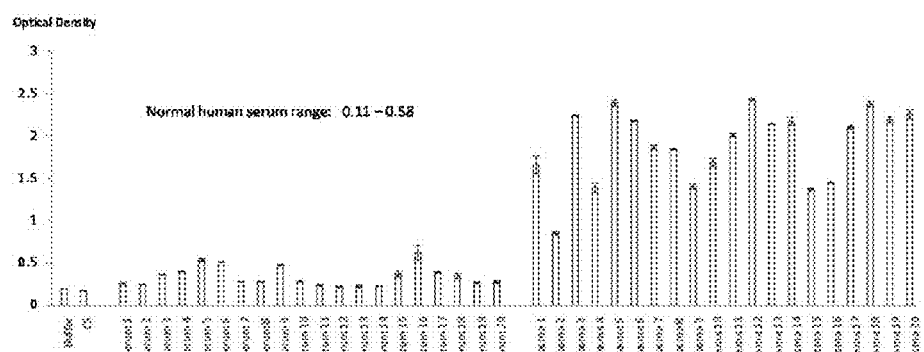
FIG. 7. Cell free nucleosome associated levels of histone variant H2AZ detected for serum and EDTA plasma samples taken from 20 healthy volunteers using the ELISA of the invention.
Figure 8:
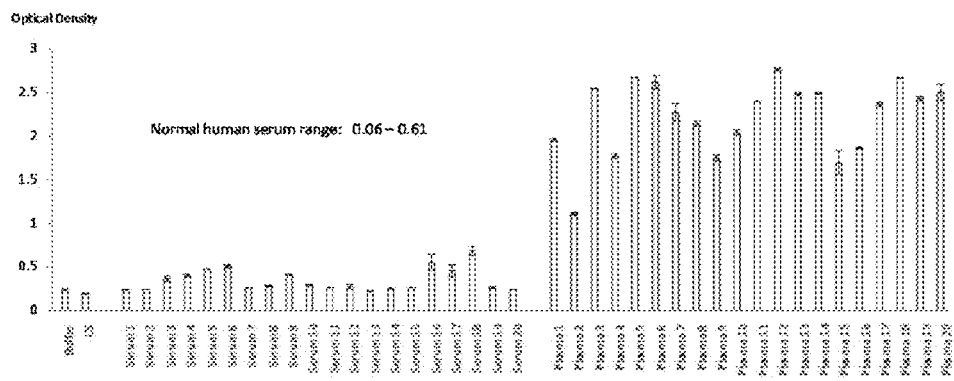
FIG. 8. Cell free nucleosome associated levels of P-H2AX(Ser139) detected for serum and EDTA plasma samples taken from 20 healthy volunteers using the ELISA of the invention.

To investigate levels of nucleosomes found in healthy subjects using the methods of the current art we measured nucleosomes in serum and plasma samples, taken from the 20 healthy subjects. Both methods of the current art produced higher signals in serum samples taken from healthy subjects than in plasma samples. The results are shown in FIG. 4. This is consistent with published data that nucleosome levels are higher in serum than plasma (*Holdenrieder et al, 2001).

Figure 9:
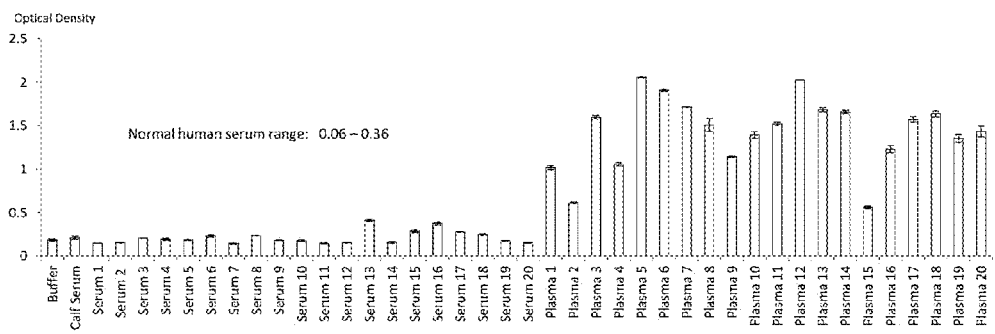
FIG. 9. Cell free nucleosome associated levels of 5-methylcytosine methylated DNA detected for serum and EDTA plasma samples taken from 20 healthy volunteers using the ELISA of the invention.
Figure 10:
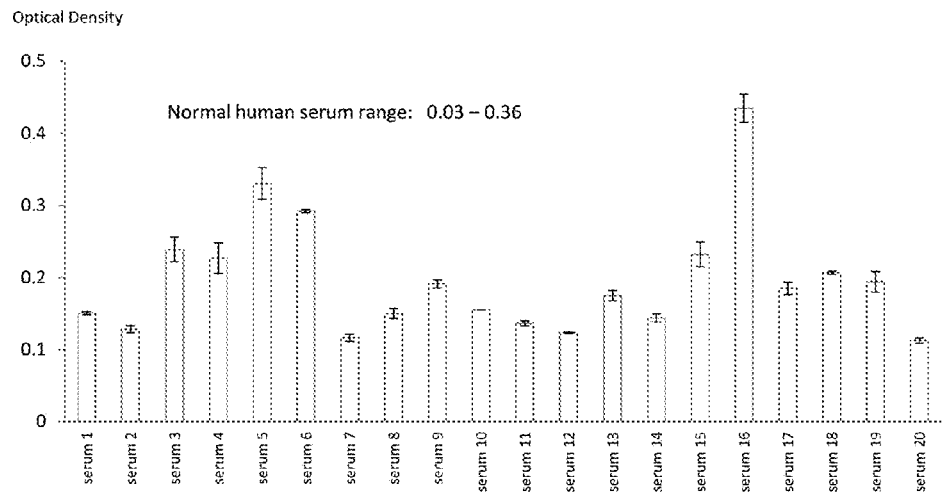
FIG. 10. Cell free nucleosome associated levels of 5-hydroxymethylcytosine methylated DNA detected for serum samples taken from 20 healthy volunteers using the ELISA of the invention.
Figure 11:
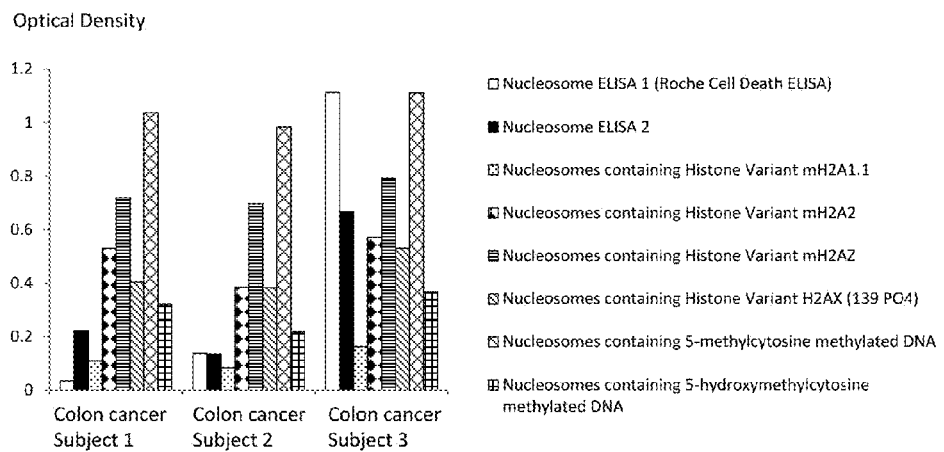
FIG. 11. Cell free nucleosome associated levels of types of histones and nucleotides detected for EDTA plasma samples taken from 3 colon cancer subjects detected using ELISA methods of the invention.
Figure 12:
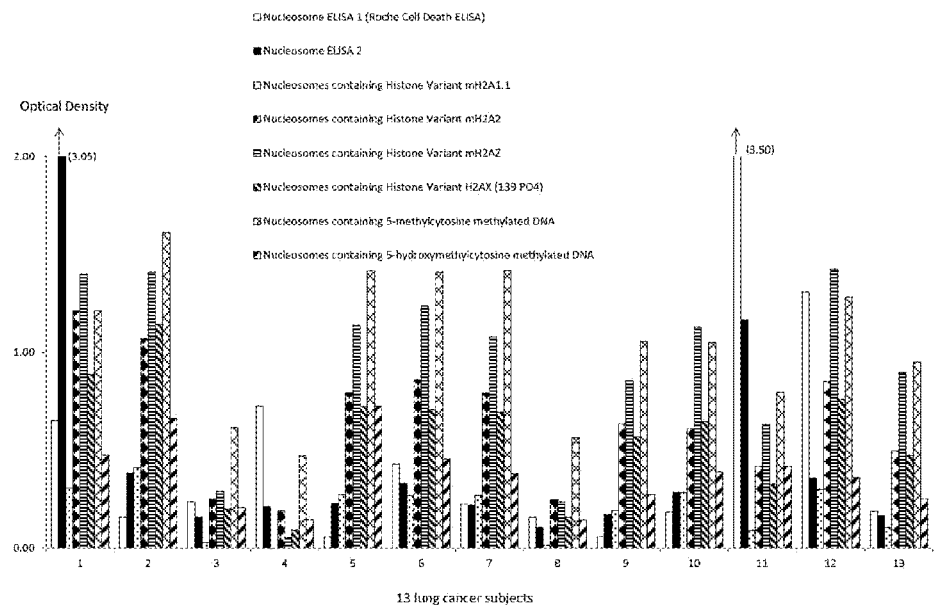
FIG. 12. Cell free nucleosome associated levels of types of histones and nucleotides detected for EDTA plasma samples taken from 13 lung cancer subjects detected using ELISA methods of the invention.
Figure 13:
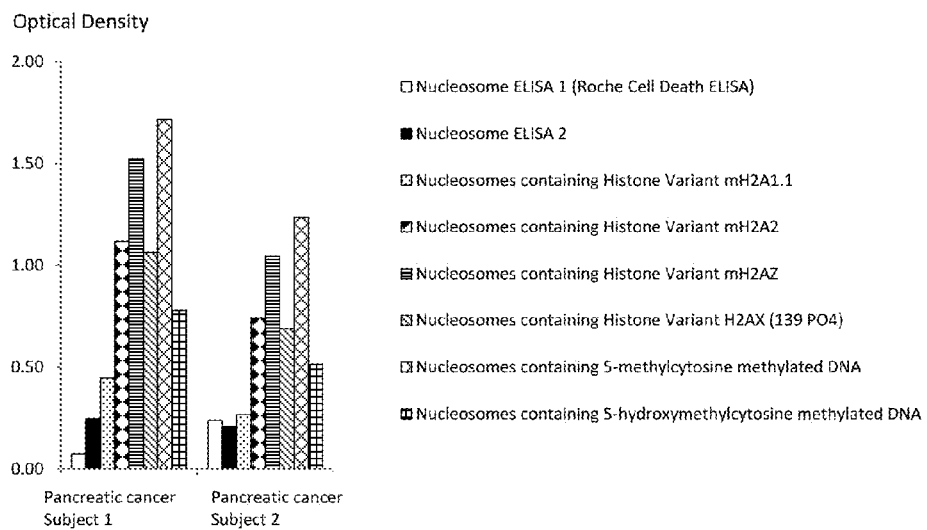
FIG. 13. Cell free nucleosome associated levels of types of histones and nucleotides detected for EDTA plasma samples taken from 2 pancreatic cancer subjects detected using ELISA methods of the invention.
Figure 14:
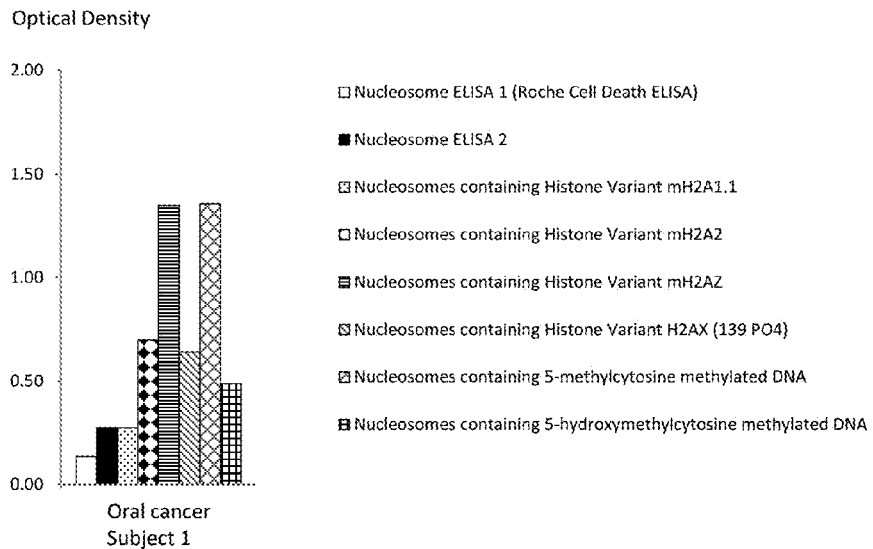
FIG. 14. Cell free nucleosome associated levels of types of histones and nucleotides detected for an EDTA plasma sample taken from 1 oral cancer subject detected using ELISA methods of the invention.

To investigate levels of nucleosomes found in healthy subjects using the methods of the invention we measured nucleosomes containing the three histone variants in the sera of 20 healthy subjects and in healthy bovine serum. The serum results for all three ELISA tests were all low or undetectable for all 20 healthy subjects. We also conducted a similar test in EDTA plasma samples, taken from the 20 healthy subjects, for the three ELISA methods of the invention and, surprisingly, higher signals were observed. High levels of cell free nucleosomes containing the histone variants mH2A1.1, mH2A2, H2AZ as well as histone P-H2AX (Ser139) were detectable by methods of the present invention in healthy human EDTA plasma but lower levels were detected in healthy human serum as shown in FIGS. 5-8. FIGS. 9 and 10 show that similar results were obtained for other nucleosome structures. This finding is unexpected and different to both the published results (*Holdenrieder et al, 2001) and the results we found for nucleosome ELISA methods of the current art. Thus, surprisingly the methods of the invention produce opposite results to methods of the current art for the relative levels of nucleosomes that occur in serum and EDTA plasma samples.

Figure 17:
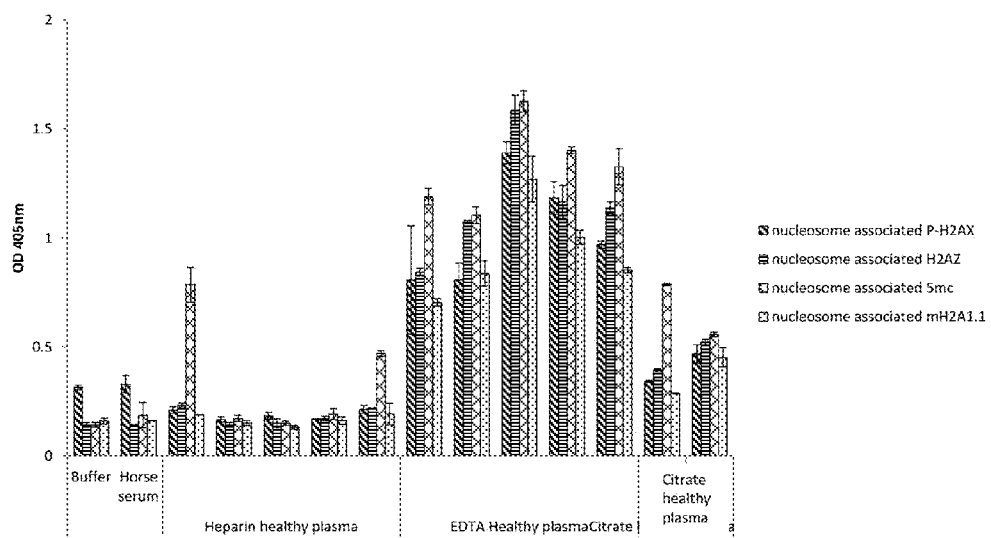
FIG. 17. Cell free nucleosome associated levels of mH2A1.1, H2AZ, P-H2AX(Ser139) and 5-methylcytosine (5mc) detected in EDTA plasma, citrate plasma and heparin plasma samples taken from healthy volunteers using the ELISA method of the invention.

We investigated whether nucleosome structures are detectable in all of the various common types of plasma that can be collected. We have found that high levels of cell free nucleosome associated H2AZ, mH2A1.1 and P-H2AX (Ser139) were detectable by the method of the invention in EDTA plasma and, to a lesser extent, in citrate plasma taken from healthy subjects, but that nucleosome associated H2AZ, mH2A1.1 and P-H2AX(Ser139) were undetectable over buffer or horse serum background signals in heparin plasma taken from healthy subjects. Some heparin plasma samples (2 of 5) were found to contain detectable levels of nucleosome associated 5-methylcytosine. The results are shown in FIG. 17. To summarise, cell free nucleosomes are found in relatively high concentrations in most or all EDTA plasma and citrate plasma samples taken from healthy subjects using the method of the invention, but are low or absent in heparin plasma or serum samples taken from healthy subjects. It is therefore clear that the precise choice of sample type will be critical for different applications.

We have shown that sample selection for the detection of cell free nucleosomes containing particular histone structures involves several parameters. These include the low levels of cell free nucleosomes generally present in serum and heparin plasma samples taken from healthy subjects, the higher levels generally present in EDTA and citrate plasma samples taken from healthy subjects, the recommendation that serum samples containing cell free nucleosomes should be stabilised by the addition of EDTA after separation of the serum from the clot (*Holdenreider et al, 2001), and the serum sampling protocol. Other stabilizing agents (for example protease inhibitors) may also be used. Where possible we used serum samples centrifuged within 1 hour of venepuncture after which 10 mM EDTA was added and the sample frozen.

Figure 18:
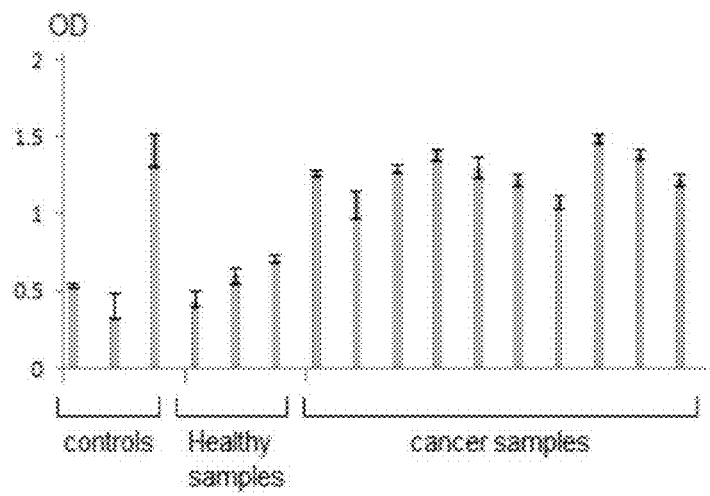
FIG. 18. Cell free nucleosome associated 5-methylcytosine levels detected for serum samples taken from 3 healthy volunteers and 10 colon cancer subjects detected using the ELISA method of the invention.

The choice of blood sample type for clinical samples should be made on the basis of optimal clinical discrimination for the particular test. Following our finding of consistently low nucleosome levels by the method of the invention in the serum of healthy subjects, we measured nucleosomes containing the histone variants mH2A1.1 and H2AZ in serum samples taken from subjects with a variety of cancer diseases. Clinical sensitivities of up to 75% for lung cancer and 80% for pancreatic cancer (FIG. 21) were observed. We also tested serum samples from cancer patients for nucleosomes containing 5-methylcytosine and observed clinical sensitivities of up to 100% as shown in FIG. 18 for colon cancer samples We also measured the relative levels of cell free nucleosomes containing various histone variants and other nucleosome structures in EDTA plasma samples taken from subjects with a variety of diseases. The levels of cell free nucleosomes are high in EDTA plasma samples taken from both healthy subjects and diseased subjects and EDTA plasma samples would therefore seem unlikely to be the best sample choice for a sensitive discriminator of diseased and healthy subjects. However, we have shown that the levels and the composition of circulating cell free nucleosomes, in terms of the relative levels of nucleosomes containing different histone variants (as well as other nucleosome structures), varies between diseased and healthy individuals and also between different diseases. We are thus the first to report both that (i) high levels of circulating nucleosomes are present in all or most EDTA plasma samples taken from both healthy and diseased subjects but this is not true of all blood sample types; and also that (ii) surprisingly, detection of disease and discrimination of disease type can none the less be made by analysis of these EDTA plasma nucleosomes on the basis of the levels and structural profile of one or more of the relative types of nucleosome structures present in the plasma of diseased and healthy subjects.

We measured cell free nucleosomes in EDTA plasma taken from healthy subjects and 117 subjects with a variety of cancer types in two experiments consisting of 55 and 62 cancer subjects respectively. In total 90% (105 of 117) of cancer samples were correctly identified as positive for cancer using the method of the invention for nucleosome associated histone variant H2AZ using a cut-off level of the mean result for healthy subjects+2 standard deviations of the mean.

Figure 19:
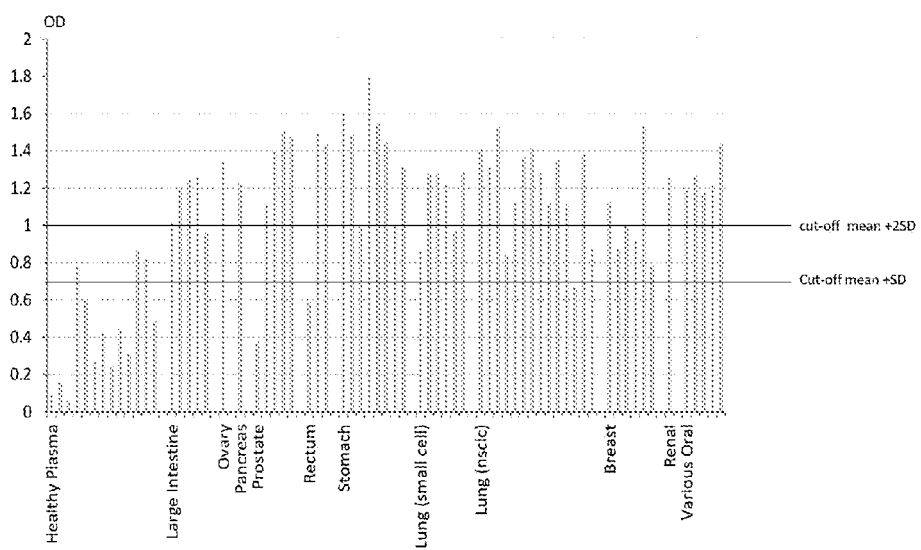
FIG. 19. Cell free nucleosome associated histone variant H2AZ levels detected for EDTA plasma samples taken from 13 healthy volunteers and 55 cancer patients. The cut-off points defined as the mean value of the healthy samples plus one or two standard deviations in the mean are shown.

In the first of these 2 experiments we measured cell free nucleosomes in EDTA plasma taken from 13 healthy subjects and 55 subjects with cancer of the stomach, large intestine, rectum, lung (small cell carcinoma and various non-small cell carcinomas), breast, ovary, prostate, kidney and various oral cancers (oral cavity, palate, pharynx and larynx). All of the samples from healthy subjects and cancer patients were positive for cell free nucleosomes. However, the levels detected in samples taken from cancer subjects were higher than found in samples from healthy subjects and the results showed that healthy and cancer subjects can be discriminated. For example the normal range calculated in OD terms as the mean±2 standard deviations in the mean, for the H2AZ nucleosome assay was 0-0.95. Using this cut-off level of 0.95; all 13 healthy subjects were negative for elevated nucleosome H2AZ levels. By contrast a positive result for elevated nucleosome H2AZ levels was found for 46 of the 55 cancer samples (an overall clinical sensitivity of 84%) including 100% (8 of 8) of stomach 100% (5 of 5) of large intestinal, 67% (2 of 3) of rectal, 83% (5 of 6) of small cell lung, 79% of non-small cell lung, 50% (3 of 6) of breast, 100% (1 of 1) of ovarian, 83% (5 of 6) of prostate, 100% (1 of 1) of kidney and 100% (5 of 5) of oral cancer samples. The results are shown in FIG. 19.

In one embodiment of the invention a control sample is provided and the cut-off level for the assay to distinguish between positive or negative results is defined in relation to the result for the control sample. This could be any proportion equal to above or below the level of the control sample result. Patient results below this level are considered negative and patient results above this level are considered positive. There may also be a "grey area" range of patient results very close to the cut-off level for which the decision is considered indeterminate and/or the test should be repeated.

Similarly for the nucleosome associated mH2A1.1 assay the normal range was 0-0.91. Using this cut-off value all 13 healthy samples were negative and 64% (35 of 55) of cancer samples were positive. For the nucleosome associated P-H2AX(Ser139) assay the normal range was 0-1.08. Using this cut-off value all 13 healthy samples were negative and 60% (33 of 55) of cancer samples were positive. Nucleosome associated 5-methylcytosine was also measured and the normal range was 0-1.41. Using this cut-off value all 13 healthy samples were negative and 55% (30 of 55) of cancer samples were positive. Thus some nucleosome assays exhibit better clinical sensitivity than others.

In addition, it is possible to use the pattern of nucleosome structures to improve the clinical utility of the invention. This may be done, for example, by lowering the cut-off point of the nucleosome associated H2AZ assay to mean+1 standard deviation which gives a range of up to 0.69. In this case the number of false negatives is reduced to 3 giving an improved clinical sensitivity of 95% (52 of 55) at the expense of an increase in false positive results for samples taken from healthy subjects from 0% to 23% (3 of 13). The results are shown in FIG. 19.

Samples found positive for H2AZ associated nucleosomes, or any nucleosomes, can be interrogated for nucleosome structure profile. The nucleosome profile can be used to distinguish between healthy and diseased patients as illustrated in FIGS. 23 and 24 where the relative proportions of various nucleosome structures in diseased patients are expressed relative to those found in healthy patients and patients with other non-cancer diseases. This shows that investigation of multiple nucleosome structures in a test panel can facilitate better clinical discrimination.

Similarly the diagnostic specificity and/or sensitivity of the invention may by increased by combining data from more than one test in the form of ratios. For example by use of the nucleosome associated H2AZ:mH2A1.1 ratio.

Thus the methods of the invention are able to detect cancer in both plasma and serum samples taken from cancer patients.

We measured the levels of circulating cell free nucleosomes containing three different histone variants in EDTA plasma samples taken from 3 patients with colon cancer, 13 patients with lung cancer, 2 patients with pancreatic cancer and 1 patient with oral cancer and compared these with the levels present in blood samples from 20 healthy subjects as well as with an artificially produced preparation of nucleosomes from healthy subjects prepared as described in the literature (*Holdenrieder et al, 2001). We have also expressed the levels observed in a normalised form as ratios of the level of nucleosomes containing different epitopes and shown that such ratios or patterns of ratios are useful for the diagnosis both of cancer in general and for the differential diagnosis of specific cancer types. We also investigated whether the level of nucleosome associated histone H2AZ varies with disease progression. We observed that the mean level of cell free nucleosomes containing histone variants increases with severity of disease and rises with increasing spread of disease to lymph nodes and with increasing tumour size and stage. This provides evidence that the nucleosomes detected are tumour associated.

We also measured the nucleosomes present in these 19 cancer samples using two nucleosome ELISA methods of the current art. Of the 19 cancer subjects studied most were found to have low EDTA plasma nucleosome levels as determined by nucleosome ELISA 1 and 2 of the current art. This result illustrates one reason why the assays of the current art are not used for routine clinical purposes.

We used ELISA methods of the present invention to measure nucleosomes containing the histone variants mH2A1.1, mH2A2 and H2AZ in the same 19 samples. Nucleosomes containing histone variants, particularly mH2A2 and H2AZ, were detectable in 16 of the 19 samples. Thus in one embodiment the invention provides a novel nucleosome ELISA method capable of detecting nucleosomes not detected by nucleosome assays of the current art.

We have also measured the levels of nucleosomes containing 2 different nucleotides and a histone PTM in the same 19 samples taken from cancer subjects as well as a sample of nucleosomes generated from healthy subjects by a method described in the literature (*Holdenrieder et al, 2001). We have used these measurements together with the nucleosome associated histone variant measurements described here, as a panel of the variety of cell free nucleosomes present in biological fluids taken from subjects with 4 different types of cancers and with nucleosomes generated from healthy subjects. Surprisingly, the pattern of nucleosomes found in the 4 types of cancer investigated (lung, colon, pancreatic and oral) were all distinguishable from that found in a nucleosome sample generated from healthy subjects. Furthermore, the different cancer types were also distinguishable from each other based on the pattern of cell free nucleosomes detectable in the blood of subjects. Thus in one embodiment of the invention there is provided a method for detecting or diagnosing the presence, type, recurrence or severity of a disease or assessing optimal drug or other treatment options by testing a sample for a panel of different nucleosome epitopes consisting of two or more measurements of nucleosomes containing different histone variants or a combination of one or more DNA histone variants and one or more histone DNA bases and/or one or more histone modifications and/or measurements of nucleosomes per se, or any combination or ratio of any of these, as an indicator of the health or disease status of a subject.

We similarly used ELISA methods of the invention to detect variability in the histone and nucleotide structures of circulating cell free nucleosomes in a variety of cancer and non-cancer diseases and compared these to the structure of nucleosomes found in 11 healthy subjects. Nucleosomes were found to be present in all the cancer and non-cancer diseases investigated and were found to have profiles that differed from those of healthy subjects.

We studied EDTA plasma samples taken from 2 cardiomyopathy patients, 10 systemic lupus erythematosus (lupus) patients, 12 ulcerative colitis patients, 10 chronic obstructive pulmonary disease (COPD) patients, 8 Crohn's disease patients and 10 rheumatoid arthritis (RA) patients and normalised the levels of various nucleosome structures as a proportion of the nucleosome associated 5-methylcytosine levels and expressed these relative to the levels found in healthy subjects. We found that the diseases were associated with nucleosome structure profiles that differed from those of healthy or cancer subjects. Thus nucleosome structure profiles can be used as a diagnostic tool for the detection, prognosis prediction, monitoring and therapeutic efficacy prediction in a wide variety of non-cancer diseases. The results are shown in FIG. 24.

We also studied the variability in structure of cell-free nucleosomes in terms of types of histones and nucleotides detected using ELISA methods of the invention for EDTA plasma samples taken from 55 patients with 10 different cancer diseases normalised as a proportion of nucleosome associated 5-methylcytosine (5mc) methylated DNA levels and expressed relative to the mean proportions found in 11 healthy subjects. We found nucleosomes present in all subjects and nucleosome structure profiles that varied between cancer diseases, non-cancer diseases and healthy subjects. Thus nucleosome structure profiles can be used as a diagnostic tool for the detection, prognosis prediction, monitoring and therapeutic efficacy prediction in cancer and other diseases. The results are shown in FIGS. 23 and 24.

Multiple isoforms or variants have been reported for histones H2A, H2B and H3. Histone H4 on the other hand is reported to exist as a single form (Tachiwana et al, 2011). It will be clear to those skilled in the art that an ELISA method of the invention using an antibody or binder targeted to bind to histone H4 will bind to virtually all nucleosomes in a sample. Thus in one embodiment the invention provides a novel method for the detection of nucleosomes per se in which nucleosomes containing a common histone variant are measured as a way of ensuring that all or most nucleotides are detected. It will further be clear to those skilled in the art that suitable antibodies or ligands produced for this application may be targeted to regions of histone H4 that are not subject to PTM modification. This will further increase the universality of the selected epitope as an epitope common to all or most nucleosomes. Similarly, it will be clear to those skilled in the art that similar suitable antibodies may be targeted to bind regions of other histone moieties selected such that the regions are common to all or most histone variants or isoforms of the said histone moiety and that are not subject to PTM (for example without limitation; common regions of histones H2A, H2B or H3). Thus the present invention described provides a means to detect all or most nucleosomes in a sample despite the variation in constituent histone isoforms and PTMs.

We conclude that the method of the present invention is a successful method for the detection and measurement of nucleosomes containing specific histone isoforms or variants, that this method can also be used as a method for the detection of nucleosomes per se and that it is a superior method for the detection of nucleosomes per se than the methods of the current art. The methods of the invention thus employed have advantages over methods for measuring nucleosomes of the current art. It will be clear to those skilled in the art that the methods of the invention can be used to detect and measure nucleosomes directly in any samples where they occur, for example in samples obtained by digestion of chromatin extracted from cells or in biological fluids such as blood, serum or plasma samples. It will also be clear that the methods described here can be developed for any histone variant or modified histone variant for which an antibody or other binder can be produced.

The invention has been tested on many cancer and non-cancer diseases and has been found effective in the detection of all the diseases tested. This includes the detection of prostate cancer cases which is reported to be undetectable by the nucleosome tests of the current art (Holdenrieder, 2001). It is clear that the invention is effective for the detection of all or most cancers. It will be clear to those skilled in the art that the clinical performance of the invention may be improved further by inclusion of further nucleosome structure tests and by examination of the ratios of different nucleosome structures present.

According to one aspect of the invention there is provided a method for detecting and measuring cell free nucleosomes containing specific histone variants or isoforms in a sample by an immunoassay which comprises the steps of:
(i) contacting the sample with an antibody or other binder which binds to a histone variant;
(ii) detecting and/or quantifying the binding of said antibody or other binder to histone variant species in the sample; and
(iii) using the presence or degree of such binding as a measure of the presence of a nucleosome associated histone variant in the sample.

According to a further aspect of the invention there is provided a double antibody, immunometric or sandwich immunoassay method for detecting and measuring cell free nucleosomes containing specific histone variants or isoforms in a sample. One embodiment of this aspect is an immunoassay which comprises the steps of:
(i) contacting the sample which may contain nucleosomes with a first antibody or other binder which binds to nucleosomes;
(ii) contacting the nucleosomes or sample with a second antibody or other binder which binds to a histone variant;
(iii) detecting and/or quantifying the binding of said second antibody or other binder to a histone variant species in the sample; and
(iv) using the presence or degree of such binding as a measure of the presence of a nucleosome associated histone variant in the sample.

According to another embodiment there is provided a method for detecting and measuring cell free nucleosomes containing specific histone variants or isoforms in a sample by an immunoassay which comprises the steps of:
(i) contacting the sample which may contain nucleosomes with a first antibody or other binder which binds to a histone variant;
(ii) contacting the nucleosomes or sample with a second antibody or other binder which binds to nucleosomes;
(iii) detecting and/or quantifying the binding of said second antibody or other binder to nucleosomes in the sample; and
(iv) using the presence or degree of such binding as a measure of the presence of a nucleosome associated histone variant in the sample.

Figure 16:
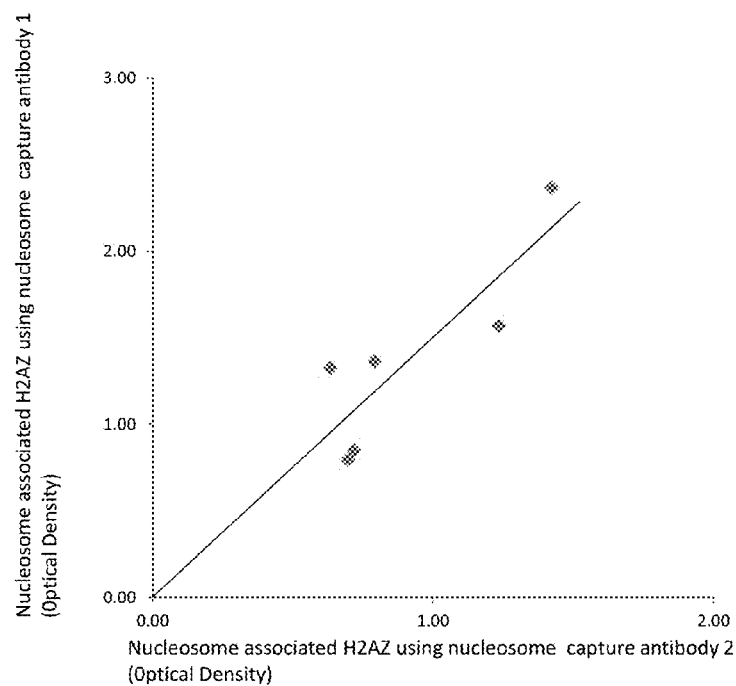
FIG. 16. Cell free nucleosome associated histone H2AZ levels of human EDTA plasma samples taken from cancer patients measured using a biotinylated anti-H2AZ detection antibody with two different monoclonal anti-histone capture antibodies.

A variety of antibodies or other binders may be employed in the invention as a binder which binds to nucleosomes. These include binders directed to bind to epitopes that occur in intact nucleosomes and not in free histones (for example; an epitope found at the junction between two histones in a nucleosome) and also binders directed to any nucleosome component including common nucleosome protein, histone or nucleic acid epitopes. We have run samples with the method of the invention using two different capture antibodies and shown that the particular capture antibody used does not materially affect the results of the method of the invention. The results are shown in FIG. 16.

It will be clear to those skilled in the art that the methods of the invention described include a variety of embodiments including classical competitive immunoassays as well as biosensor type assays and label-free assays of the type marketed for example by ForteBio Incorporated of USA which may be immunometric in nature.

According to one embodiment of the invention there is provided a method for detecting and measuring a histone isoform or variant, or a nucleosome associated histone isoform or variant, in a sample by a label-free immunometric immunoassay which comprises the steps of:
(i) contacting the sample with an antibody or other binder which binds to a histone isoform or variant;
(ii) detecting and/or quantifying the binding of said antibody or other binder to a histone isoform or variant in the sample; and (iii) using the presence or degree of such binding as a measure of the presence of a histone isoform or variant or a nucleosome associated histone isoform or variant in the sample.

According to a further embodiment of the invention there is provided a method for detecting and measuring a cell free histone isoform or variant, or a nucleosome associated histone isoform or variant, in a sample by a competitive immunoassay which comprises the steps of:
  (i) contacting the sample with an antibody or other binder which binds to a histone isoform or variant;
  (ii) detecting and/or quantifying the binding of said antibody or other binder to a histone isoform or variant in the sample; and
  (iii) using the presence or degree of such binding as a measure of the presence of a histone isoform or variant in the sample.

According to a further aspect of the invention there is provided a method for detecting the proportion of nucleosomes that comprises a histone isoform in a sample comprising the steps of:
  (i) detecting or measuring the level of nucleosomes in a sample;
  (ii) detecting or measuring the level of a nucleosome associated histone isoform according to a method of the invention; and
  (iii) using the two measurements to determine the proportion of nucleosomes that contain the histone isoform.

According to one embodiment of this aspect of the invention; both the total nucleosome level in the sample and the nucleosome associated histone variant level of interest are measured using the method of the invention. In another embodiment nucleosome ELISA methods of the current art are used to determine total nucleosome levels. In yet another embodiment a measure of total DNA is used as a proxy for total nucleosome level.

We have shown that the detection and measurement of nucleosomes containing histone variants in the blood taken from subjects can be used as a diagnostic method to identify subjects with cancer and to differentiate them from healthy subjects. Furthermore we have shown that the patterns of nucleosomes containing a panel of different histone variants, nucleotides and histone PTMs can be used to distinguish between different cancers. It will be clear to those skilled in the art that this provides the basis for a cancer blood test that will detect cancer in subjects and can be used to distinguish between cancer types in cancer positive subjects. According to a another aspect of the invention there is provided a method for detecting or diagnosing the presence of a disease by measuring or detecting the presence and/or the level or concentration of cell free nucleosomes containing a histone variant in a body fluid, and using the detected level as a biomarker of the disease status of a subject including, without limitation, a clinical diagnosis of a disease, a differential diagnosis of disease type or subtype, or a disease prognosis, or a disease relapse, or a diagnosis of subject susceptibility to treatment regimens. It will be appreciated by those skilled in the art that body fluids used for diagnostic testing include without limitation blood, serum, plasma, urine, cerebrospinal fluid and other fluids. In a preferred embodiment the body fluid selected as the sample is blood, serum or plasma. The assay response level, concentration or quantity of a nucleosome associated histone variant in a body fluid may be expressed in absolute terms or relative terms, for example, without limitation, as a proportion of the total nucleosome or total DNA level present or as a ratio to the level of nucleosomes containing another histone variant or nucleotide or PTM.

According to a further aspect of the invention there is provided a method for detecting or measuring the presence and/or the level of nucleosomes containing a particular histone variant in a cell which comprises the steps of:
  (i) isolating chromatin from a cell;
  (ii) breaking down the chromatin to form mono-nucleosomes and/or oligo-nucleosomes; and
  (iii) detecting or measuring the presence of a histone variant in the mono-nucleosomes and/or oligo-nucleosomes by means of an immunoassay method as described herein.

Methods for producing mono-nucleosomes and/or oligo-nucleosomes from chromatin are well known in the art and include enzyme digestion and sonication (Dai et al, 2011). We have produced cell free nucleosomes from MCF7 cells using standard procedures and used the method of the invention to show that these MCF7 nucleosomes do include nucleosomes containing the histone variants mH2A1.1, H2AZ as well as P-H2AX(Ser139).

In one embodiment the histone variant selected for detection by the method is a commonly occurring isoform that occurs in all or most intact nucleosomes, providing a method for the detection or measurement of nucleosomes per se. In another embodiment the epitope on a histone isoform selected for detection by the method is located at a region of the histone isoform that is common to, and occurs in, all or most isoforms of the said histone and hence in all or most intact nucleosomes and is further not subject to PTM, providing a method for the detection or measurement of nucleosomes per se.

It will be appreciated by those skilled in the art that the described method of detecting nucleosome associated histone variants in cells or tissues is simpler, faster, cheaper, more quantitative and/or more reproducible than currently used methods including IHC, Western Blotting or FACS. The level, concentration or quantity of a particular nucleosome associated histone variant may be expressed in absolute terms or relative terms, for example as a proportion of the total nucleosomes or total DNA present or as a ratio to the level of nucleosomes containing another histone variant or PTM or nucleotide.

It will be clear to those skilled in the art that the terms antibody, binder or ligand in regard to any aspect of the invention is not limiting but intended to include any binder capable of binding to specific molecules or entities and that any suitable binder can be used in the method of the invention. It will also be clear that the term nucleosomes is intended to include mononucleosomes and oligonucleosomes and any such chromatin fragments that can be analysed in fluid media.

According to another aspect of the invention there is provided a kit for detecting or measuring nucleosomes which comprises a ligand or binder specific for the histone variant or a component part thereof, or a structural/shape mimic of the nucleosome or component part thereof, together with instructions for use of the kit in accordance with any of the methods defined herein.

According to a further aspect of the invention there is provided a kit for detecting or measuring nucleosomes containing a particular histone variant which comprises a ligand or binder specific for the histone variant or a component part thereof, or a structural/shape mimic of the nucleosome or component part thereof, together with instructions for use of the kit in accordance with any of the methods defined herein.

According to another aspect of the invention there is provided a method for identifying a histone variant biomarker for detecting or diagnosing disease status in animals or humans which comprises the steps of:
(i) detecting or measuring the level of cell free nucleosomes containing a histone variant in a body fluid of diseased subjects;
(ii) detecting or measuring the level of cell free nucleosomes containing a histone variant in a body fluid of control subjects; and
(iii) using the difference between the levels detected in diseased and control subjects to identify whether a particular histone variant is useful as a biomarker for that disease.

It will be clear to those skilled in the art that the control subjects may be selected on a variety of basis which may include, for example, subjects known to be free of the disease or may be subjects with a different disease (for example; for the investigation of differential diagnosis).

According to a further aspect of the invention there is provided a method for identifying a histone variant biomarker for assessing the prognosis of a diseased animal or human subject which comprises the steps of:
(i) detecting or measuring the level of cell free nucleosomes containing a histone variant in a body fluid of diseased subjects; and
(ii) correlating the level of cell free nucleosomes containing a histone variant detected in a body fluid of diseased subjects with the disease outcome of the subjects.

According to a further aspect of the invention there is provided a method for identifying a histone variant biomarker to be used for the selection of a treatment regimen for a diseased animal or human subject in need of treatment which comprises the steps of:
(i) detecting or measuring the level of cell free nucleosomes containing a histone variant in a body fluid of diseased subjects; and
(ii) correlating the level of cell free nucleosomes containing a histone variant detected in a body fluid of diseased subjects with the observed efficacy of a treatment regimen in those subjects.

According to a further aspect of the invention there is provided a method for identifying a histone variant biomarker to be used for monitoring the treatment of a diseased animal or human subject which comprises the steps of:
(i) detecting or measuring the level of cell free nucleosomes containing a histone variant in a body fluid of a diseased subject;
(ii) repeating said detection or measurement on one or more occasions during the disease progression of the subject; and
(iii) correlating the level of cell free nucleosomes containing a histone variant detected in a body fluid of a diseased subject with the disease progression in the subject.

According to a further aspect of the invention, there is provided a biomarker identified by the method as defined herein.

It will be clear to those skilled in the art that cell free nucleosomes containing a histone variant can also be detected in a biological fluid including blood, plasma, serum and urine by a procedure involving the extraction of the histone variant protein from the nucleosome complex followed by a method for the detection or quantification of the extracted free histone variant protein. Suitable extraction procedures include commonly used acid extraction procedures for histones which utilise the basic nature of histones proteins. The detection of the free histone variant may be performed, for example, by an immunoassay for the free histone moiety. Thus in one embodiment of the invention a histone variant is extracted from a biological fluid including blood, plasma, serum and urine and the extract is tested for the presence of a histone variant.

It is known in the art that one may detect the presence of a protein that is comprised as part of a complex containing other moieties by immunoassay methods. It will be clear to those skilled in the art that cell free nucleosomes containing a histone variant can be detected in a biological fluid including blood, plasma, serum and urine by a procedure involving the direct immunoassay of the histone variant itself in the fluid. In this procedure a single antibody immunoassay, utilising an antibody directed to an epitope present on a histone variant, or a 2-site immunoassay, utilising two antibodies directed to two epitopes present on a histone variant, is used to detect the presence of a histone variant within a nucleosome. Thus in another embodiment of the invention a histone variant contained within a nucleosome is detected directly in a biological fluid including blood, plasma, serum and urine by use of an immunoassay method for a histone variant.

Thus in one embodiment of the invention a histone variant is extracted from a biological fluid including blood, plasma, serum and urine and the extract is tested for the presence of a histone variant.

A further aspect of the invention provides ligands or binders, such as naturally occurring or chemically synthesised compounds, capable of specific binding to the biomarker. A ligand or binder according to the invention may comprise a peptide, an antibody or a fragment thereof, or a synthetic ligand such as a plastic antibody, or an aptamer or oligonucleotide, capable of specific binding to the biomarker. The antibody can be a monoclonal antibody or a fragment thereof capable of specific binding to the biomarker. A ligand according to the invention may be labeled with a detectable marker, such as a luminescent, fluorescent, enzyme or radioactive marker; alternatively or additionally a ligand according to the invention may be labeled with an affinity tag, e.g. a biotin, avidin, streptavidin or His (e.g. hexa-His) tag. Alternatively ligand binding may be determined using a label-free technology for example that of ForteBio Inc.

A biosensor according to the invention may comprise the biomarker or a structural/shape mimic thereof capable of specific binding to an antibody against the biomarker. Also provided is an array comprising a ligand or mimic as described herein.

Also provided by the invention is the use of one or more ligands as described herein, which may be naturally occurring or chemically synthesised, and is suitably a peptide, antibody or fragment thereof, aptamer or oligonucleotide, or the use of a biosensor of the invention, or an array of the invention, or a kit of the invention to detect and/or quantify the biomarker. In these uses, the detection and/or quantification can be performed on a biological sample as defined herein.

Diagnostic or monitoring kits are provided for performing methods of the invention. Such kits will suitably comprise a ligand according to the invention, for detection and/or quantification of the biomarker, and/or a biosensor, and/or an array as described herein, optionally together with instructions for use of the kit.

A further aspect of the invention is a kit for detecting the presence of a disease state, comprising a biosensor capable of detecting and/or quantifying one or more of the biomarkers as defined herein.

Biomarkers for detecting the presence of a disease are essential targets for discovery of novel targets and drug molecules that retard or halt progression of the disorder. As the level of the biomarker is indicative of disorder and of drug response, the biomarker is useful for identification of novel therapeutic compounds in in vitro and/or in vivo assays. Biomarkers of the invention can be employed in methods for screening for compounds that modulate the activity of the biomarker.

Thus, in a further aspect of the invention, there is provided the use of a binder or ligand, as described, which can be a peptide, antibody or fragment thereof or aptamer or oligonucleotide according to the invention; or the use of a biosensor according to the invention, or an array according to the invention; or a kit according to the invention, to identify a substance capable of promoting and/or of suppressing the generation of the biomarker.

Also there is provided a method of identifying a substance capable of promoting or suppressing the generation of the biomarker in a subject, comprising administering a test substance to a subject animal and detecting and/or quantifying the level of the biomarker present in a test sample from the subject.

The term "biomarker" means a distinctive biological or biologically derived indicator of a process, event, or condition. Biomarkers can be used in methods of diagnosis, e.g. clinical screening, and prognosis assessment and in monitoring the results of therapy, identifying patients most likely to respond to a particular therapeutic treatment, drug screening and development. Biomarkers and uses thereof are valuable for identification of new drug treatments and for discovery of new targets for drug treatment.

The terms "detecting" and "diagnosing" as used herein encompass identification, confirmation, and/or characterisation of a disease state. Methods of detecting, monitoring and of diagnosis according to the invention are useful to confirm the existence of a disease, to monitor development of the disease by assessing onset and progression, or to assess amelioration or regression of the disease. Methods of detecting, monitoring and of diagnosis are also useful in methods for assessment of clinical screening, prognosis, choice of therapy, evaluation of therapeutic benefit, i.e. for drug screening and drug development.

Efficient diagnosis and monitoring methods provide very powerful "patient solutions" with the potential for improved prognosis, by establishing the correct diagnosis, allowing rapid identification of the most appropriate treatment (thus lessening unnecessary exposure to harmful drug side effects), and reducing relapse rates.

In one embodiment, said biomarker is released from the cells of a tumour. Thus, according to a further aspect of the invention there is provided a method for the detection of a tumour growth which comprises the steps of (i) measuring a biomarker in a biological sample that is associated with or released from the cells of a tumour and (ii) demonstrating that the level of said biomarker is associated with the size, stage, aggressiveness or dissemination of the tumour.

It is known that increased cell turnover, cell death and apoptosis lead to increased circulatory levels of cell free nucleosomes (Holdenrieder et al, 2001). Circulating cell free nucleosomes level is a non-specific indicator and occurs in a variety of conditions including inflammatory diseases, a large variety of benign and malignant conditions, autoimmune diseases, as well as following trauma or ischaemia (Holdenrieder et al 2001). It will be clear to those skilled in the art that the invention will have application in a variety of disease areas where circulating nucleosomes have been found in subjects. These include, without limitation, trauma (for example; severe injury or surgery), extreme exercise (for example running a marathon), stroke and heart attack and sepsis or other serious infection. We have used the immunoassay method of the invention to measure nucleosome levels and investigate their histone and nucleotide structure variability in a variety of such diseases including cardiomyopathy, systemic lupus erythematosus, ulcerative colitis, chronic obstructive pulmonary disease, Crohn's disease and rheumatoid arthritis and compared these with the results of healthy subjects. We can detect nucleosomes and determine their relative structures (in terms of histone and nucleotide composition) in all these diseases. As methods of the current invention are capable of detection of a wider range of nucleosomes than current nucleosome ELISA methods, the methods of the invention have applications in a wide range of cancer and non-cancer disease areas.

The immunoassays of the invention include immunometric assays employing enzyme detection methods (for example ELISA), fluorescence labelled immunometric assays, time-resolved fluorescence labelled immunometric assays, chemiluminescent immunometric assays, immunoturbidimetric assays, particulate labelled immunometric assays and immunoradiometric assays and competitive immunoassay methods including labelled antigen and labelled antibody competitive immunoassay methods with a variety of label types including radioactive, enzyme, fluorescent, time-resolved fluorescent and particulate labels. All of said immunoassay methods are well known in the art, see for example Salgame et al, 1997 and van Nieuwenhuijze et al, 2003.

In one embodiment, said biological sample comprises a body fluid. For example, biological samples that may be tested in a method of the invention include cerebrospinal fluid (CSF), whole blood, blood serum, plasma, menstrual blood, endometrial fluid, urine, saliva, or other bodily fluid (stool, tear fluid, synovial fluid, sputum), breath, e.g. as condensed breath, or an extract or purification therefrom, or dilution thereof. Biological samples also include specimens from a live subject, or taken post-mortem. The samples can be prepared, for example where appropriate diluted or concentrated, and stored in the usual manner.

In one embodiment, the method of the invention is repeated on multiple occasions. This embodiment provides the advantage of allowing the detection results to be monitored over a time period. Such an arrangement will provide the benefit of monitoring or assessing the efficacy of treatment of a disease state. Such monitoring methods of the invention can be used to monitor onset, progression, stabilisation, amelioration, relapse and/or remission.

Thus, the invention also provides a method of monitoring efficacy of a therapy for a disease state in a subject, suspected of having such a disease, comprising detecting and/or quantifying the biomarker present in a biological sample from said subject. In monitoring methods, test samples may be taken on two or more occasions. The method may further comprise comparing the level of the biomarker(s) present in the test sample with one or more control(s) and/or with one or more previous test sample(s) taken earlier from the same test subject, e.g. prior to commencement of therapy, and/or from the same test subject at an earlier stage of therapy. The method may comprise detecting a change in the nature or amount of the biomarker(s) in test samples taken on different occasions.

Thus, according to a further aspect of the invention, there is provided a method for monitoring efficacy of therapy for a disease state in a human or animal subject, comprising:
(i) quantifying the amount of the biomarker as defined herein; and
(ii) comparing the amount of said biomarker in a test sample with the amount present in one or more control(s) and/or one or more previous test sample(s) taken at an earlier time from the same test subject.

A change in the level of the biomarker in the test sample relative to the level in a previous test sample taken earlier from the same test subject may be indicative of a beneficial effect, e.g. stabilisation or improvement, of said therapy on the disorder or suspected disorder. Furthermore, once treatment has been completed, the method of the invention may be periodically repeated in order to monitor for the recurrence of a disease.

Methods for monitoring efficacy of a therapy can be used to monitor the therapeutic effectiveness of existing therapies and new therapies in human subjects and in non-human animals (e.g. in animal models). These monitoring methods can be incorporated into screens for new drug substances and combinations of substances.

In a further embodiment the monitoring of more rapid changes due to fast acting therapies may be conducted at shorter intervals of hours or days.

According to a further aspect of the invention, there is provided a method for identifying a biomarker for detecting the presence of a disease state. The term "identifying" as used herein means confirming the presence of the biomarker present in the biological sample. Quantifying the amount of the biomarker present in a sample may include determining the concentration of the biomarker present in the sample. Identifying and/or quantifying may be performed directly on the sample, or indirectly on an extract therefrom, or on a dilution thereof.

In alternative aspects of the invention, the presence of the biomarker is assessed by detecting and/or quantifying antibody or fragments thereof capable of specific binding to the biomarker that are generated by the subject's body in response to the biomarker and thus are present in a biological sample from a subject having a disease state.

Identifying and/or quantifying can be performed by any method suitable to identify the presence and/or amount of a specific protein in a biological sample from a patient or a purification or extract of a biological sample or a dilution thereof. In methods of the invention, quantifying may be performed by measuring the concentration of the biomarker in the sample or samples. Biological samples that may be tested in a method of the invention include those as defined hereinbefore. The samples can be prepared, for example where appropriate diluted or concentrated, and stored in the usual manner.

Identification and/or quantification of biomarkers may be performed by detection of the biomarker or of a fragment thereof, e.g. a fragment with C-terminal truncation, or with N-terminal truncation. Fragments are suitably greater than 4 amino acids in length, for example 5, 6, 7, 8, 9, 10, 11, 12, 13, 14, 15, 16, 17, 18, 19, or 20 amino acids in length. It is noted in particular that peptides of the same or related sequence to that of histone tails are particularly useful fragments of histone proteins.

The biomarker may be directly detected, e.g. by SELDI or MALDI-TOF. Alternatively, the biomarker may be detected directly or indirectly via interaction with a ligand or ligands such as an antibody or a biomarker-binding fragment thereof, or other peptide, or ligand, e.g. aptamer, or oligonucleotide, capable of specifically binding the biomarker. The ligand or binder may possess a detectable label, such as a luminescent, fluorescent or radioactive label, and/or an affinity tag.

For example, detecting and/or quantifying can be performed by one or more method(s) selected from the group consisting of: SELDI (-TOF), MALDI (-TOF), a 1-D gel-based analysis, a 2-D gel-based analysis, Mass spec (MS), reverse phase (RP) LC, size permeation (gel filtration), ion exchange, affinity, HPLC, UPLC and other LC or LC MS-based techniques. Appropriate LC MS techniques include ICAT® (Applied Biosystems, CA, USA), or iTRAQ® (Applied Biosystems, CA, USA). Liquid chromatography (e.g. high pressure liquid chromatography (HPLC) or low pressure liquid chromatography (LPLC)), thin-layer chromatography, NMR (nuclear magnetic resonance) spectroscopy could also be used.

Methods of diagnosing or monitoring according to the invention may comprise analysing a sample by SELDI TOF or MALDI TOF to detect the presence or level of the biomarker. These methods are also suitable for clinical screening, prognosis, monitoring the results of therapy, identifying patients most likely to respond to a particular therapeutic treatment, for drug screening and development, and identification of new targets for drug treatment.

Identifying and/or quantifying the analyte biomarkers may be performed using an immunological method, involving an antibody, or a fragment thereof capable of specific binding to the biomarker. Suitable immunological methods include sandwich immunoassays, such as sandwich ELISA, in which the detection of the analyte biomarkers is performed using two antibodies which recognize different epitopes on a analyte biomarker; radioimmunoassays (RIA), direct, indirect or competitive enzyme linked immunosorbent assays (ELISA), enzyme immunoassays (EIA), Fluorescence immunoassays (FIA), western blotting, immunoprecipitation and any particle-based immunoassay (e.g. using gold, silver, or latex particles, magnetic particles, or Q-dots). Immunological methods may be performed, for example, in microtitre plate or strip format.

In one embodiment, one or more of the biomarkers may be replaced by a molecule, or a measurable fragment of the molecule, found upstream or downstream of the biomarker in a biological pathway.

The identification of key biomarkers specific to a disease is central to integration of diagnostic procedures and therapeutic regimes. Using predictive biomarkers appropriate diagnostic tools such as biosensors can be developed; accordingly, in methods and uses of the invention, identifying and quantifying can be performed using a biosensor, microanalytical system, microengineered system, microseparation system, immunochromatography system or other suitable analytical devices. The biosensor may incorporate an immunological method for detection of the biomarker(s), electrical, thermal, magnetic, optical (e.g. hologram) or acoustic technologies. Using such biosensors, it is possible to detect the target biomarker(s) at the anticipated concentrations found in biological samples.

As used herein, the term "biosensor" means anything capable of detecting the presence of the biomarker. Examples of biosensors are described herein.

Biosensors according to the invention may comprise a ligand binder or ligands, as described herein, capable of specific binding to the biomarker. Such biosensors are useful in detecting and/or quantifying a biomarker of the invention.

The biomarker(s) of the invention can be detected using a biosensor incorporating technologies based on "smart" holograms, or high frequency acoustic systems, such systems are particularly amenable to "bar code" or array configurations.

In smart hologram sensors (Smart Holograms Ltd, Cambridge, UK), a holographic image is stored in a thin polymer film that is sensitised to react specifically with the biomarker. On exposure, the biomarker reacts with the polymer leading to an alteration in the image displayed by the hologram. The test result read-out can be a change in the optical brightness, image, colour and/or position of the image. For qualitative and semi-quantitative applications, a sensor hologram can be read by eye, thus removing the need for detection equipment. A simple colour sensor can be used to read the signal when quantitative measurements are required. Opacity or colour of the sample does not interfere with operation of the sensor. The format of the sensor allows multiplexing for simultaneous detection of several substances. Reversible and irreversible sensors can be designed to meet different requirements, and continuous monitoring of a particular biomarker of interest is feasible.

Suitably, biosensors for detection of one or more biomarkers of the invention combine biomolecular recognition with appropriate means to convert detection of the presence, or quantitation, of the biomarker in the sample into a signal. Biosensors can be adapted for "alternate site" diagnostic testing, e.g. in the ward, outpatients' department, surgery, home, field and workplace.

Biosensors to detect one or more biomarkers of the invention include acoustic, plasmon resonance, holographic, Bio-Layer Interferometry (BLI) and microengineered sensors. Imprinted recognition elements, thin film transistor technology, magnetic acoustic resonator devices and other novel acousto-electrical systems may be employed in biosensors for detection of the one or more biomarkers of the invention.

Methods involving identification and/or quantification of one or more biomarkers of the invention can be performed on bench-top instruments, or can be incorporated onto disposable, diagnostic or monitoring platforms that can be used in a non-laboratory environment, e.g. in the physician's office or at the patient's bedside. Suitable biosensors for performing methods of the invention include "credit" cards with optical or acoustic readers. Biosensors can be configured to allow the data collected to be electronically transmitted to the physician for interpretation and thus can form the basis for e-medicine.

Diagnostic kits for the diagnosis and monitoring of the presence of a disease state are described herein. In one embodiment, the kits additionally contain a biosensor capable of identifying and/or quantifying a biomarker. Suitably a kit according to the invention may contain one or more components selected from the group: a ligand binder, or ligands, specific for the biomarker or a structural/shape mimic of the biomarker, one or more controls, one or more reagents and one or more consumables; optionally together with instructions for use of the kit in accordance with any of the methods defined herein.

The identification of biomarkers for a disease state permits integration of diagnostic procedures and therapeutic regimes. Detection of a biomarker of the invention can be used to screen subjects prior to their participation in clinical trials. The biomarkers provide the means to indicate therapeutic response, failure to respond, unfavourable side-effect profile, degree of medication compliance and achievement of adequate serum drug levels. The biomarkers may be used to provide warning of adverse drug response. Biomarkers are useful in development of personalized therapies, as assessment of response can be used to fine-tune dosage, minimise the number of prescribed medications, reduce the delay in attaining effective therapy and avoid adverse drug reactions. Thus by monitoring a biomarker of the invention, patient care can be tailored precisely to match the needs determined by the disorder and the pharmacogenomic profile of the patient, the biomarker can thus be used to titrate the optimal dose, predict a positive therapeutic response and identify those patients at high risk of severe side effects.

Biomarker-based tests provide a first line assessment of 'new' patients, and provide objective measures for accurate and rapid diagnosis, not achievable using the current measures.

Furthermore, diagnostic biomarker tests are useful to identify family members or patients with mild or asymptomatic disease or who may be at high risk of developing symptomatic disease. This permits initiation of appropriate therapy, or preventive measures, e.g. managing risk factors. These approaches are recognised to improve outcome and may prevent overt onset of the disorder.

Biomarker monitoring methods, biosensors and kits are also vital as patient monitoring tools, to enable the physician to determine whether relapse is due to worsening of the disorder. If pharmacological treatment is assessed to be inadequate, then therapy can be reinstated or increased; a change in therapy can be given if appropriate. As the biomarkers are sensitive to the state of the disorder, they provide an indication of the impact of drug therapy.

The invention will now be illustrated with reference to the following non-limiting examples.

EXAMPLE 1

Figure 1:
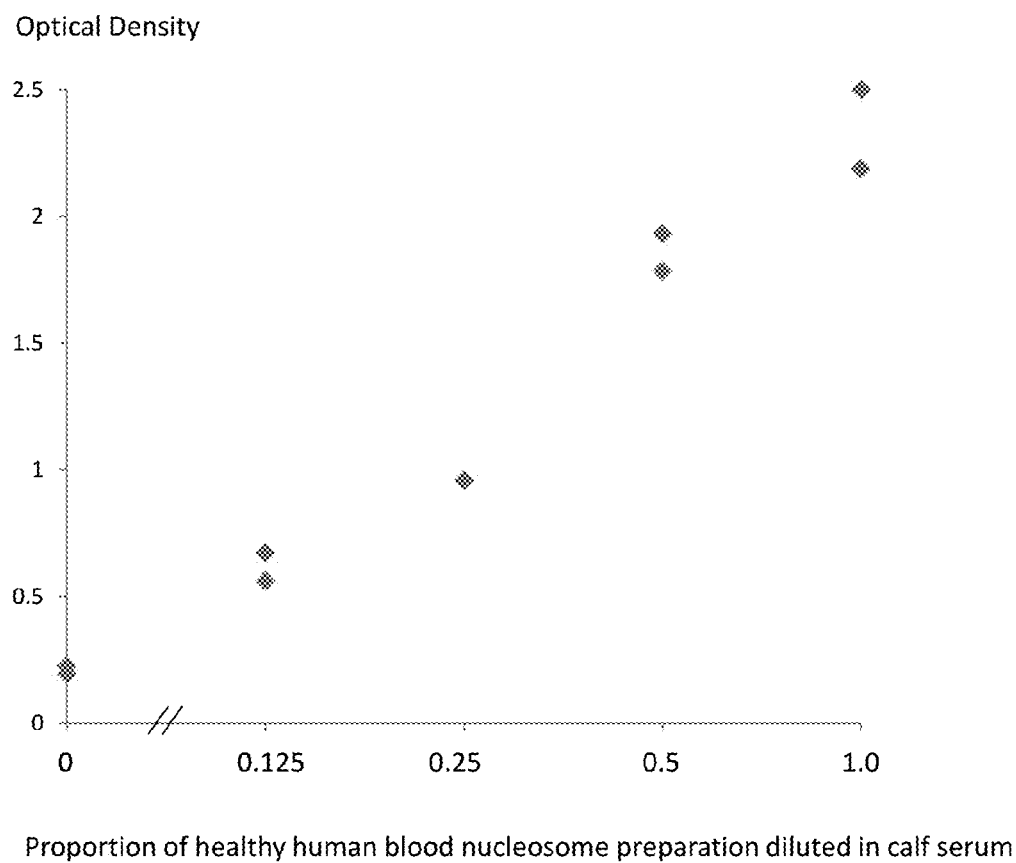
FIG. 1. ELISA dose response curve for the detection of human cell free nucleosomes prepared by a published method (*Holdenrieder et al, 2001) containing histone variant macroH2A1.1 diluted into calf serum.

A human blood sample containing cell free nucleosomes from healthy subjects prepared according to the method described by Holdenrieder (*Holdenrieder et al, 2001) was tested using an ELISA for the nucleosome associated histone variant macroH2A1.1 using a solid phase anti-histone capture antibody that binds intact nucleosomes and a biotinylated affinity purified polyclonal anti-histone variant macroH2A1.1 detection antibody. The human sample was serially diluted in fetal calf serum and was tested in duplicate in the ELISA undiluted and at dilutions of 1:2, 1:4, and 1:8. Neat fetal calf serum was also run in the ELISA as a control sample containing no cell free nucleosomes. The assay method was as follows: A solution of anti-histone antibody in 0.1M phosphate buffer pH 7.4 was added to microtitre wells (100 µL/well) and incubated overnight at 4° C. to coat the wells with capture antibody. Excess anti-histone antibody was decanted. A solution of bovine serum albumin (20 g/L) was added to the wells (150 µL/well) and incubated 60 minutes at room temperature to block excess protein binding sites on the wells. Excess bovine serum albumin solution was decanted and the wells were washed twice with wash buffer (200 µL/well, 0.05M TRIS/HCl buffer pH 7.5 containing 1% Tween 20). Sample (10 µL/well) and assay buffer (50 µL/well, 0.05M TRIS/HCl pH 7.5 containing 0.9% NaCl, 0.05% sodium deoxycholate and 1% Nonidet P40 substitute) were added to the wells and incubated 90 minutes at room temperature with mild agitation. The sample and assay buffer mixture was decanted and the wells were washed three times with wash buffer (200 µL/well). A solution of biotinylated affinity purified polyclonal anti-histone variant macroH2A1.1 detection antibody was added (50 μL/well) and incubated 90 minutes at room temperature with mild agitation. Excess detection antibody was decanted and the wells were again washed three times with wash buffer (200 μL/well). A solution containing a streptavidin-horse radish peroxidase conjugate was added (50 μL/well) and incubated 30 minutes at room temperature with mild agitation. Excess conjugate was decanted and the wells were again washed three times with wash buffer (200 μL/well). A coloured substrate solution (100 μL/well, 2,2'-Azinobis [3-ethylbenzothiazoline-6-sulfonic acid]-diammonium salt) was added and incubated 30 minutes at room temperature with mild agitation. A STOP solution (100 μL/well) containing 1% sodium dodecyl sulphate was added and the optical density (OD) of the wells was measured at a wavelength of 405 nm using a standard microtitre plate reader. A reproducible dose response curve of increasing colour with increasing nucleosome associated histone variant macroH2A1.1 concentration was observed with a low background signal observed in the absence of nucleosome associated histone variant macroH2A1.1 (fetal calf serum). The positive ELISA signal indicates that the histone variant macroH2A1.1 detected by the ELISA is incorporated within a nucleosome as the capture antibody used binds to histones within intact nucleosomes and does not bind to histone H2. The results are shown in FIG. 1.

EXAMPLE 2

Figure 2:
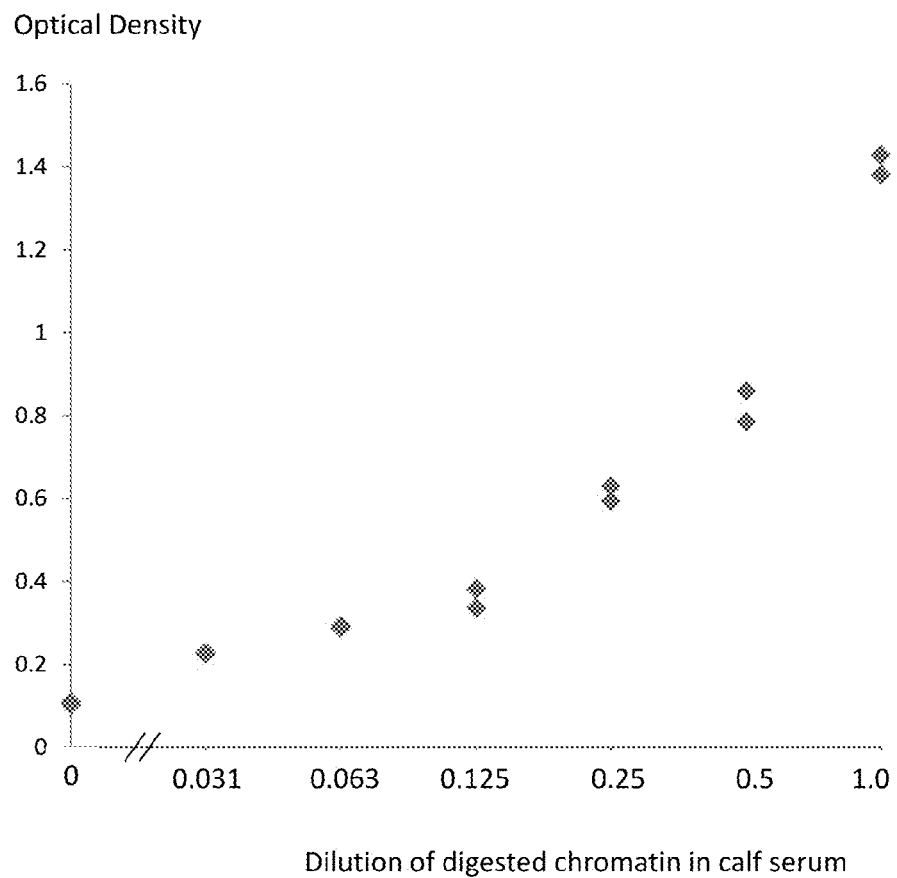
FIG. 2. ELISA dose response curve for the detection of histone variant macroH2A2 in cell free nucleosomes in cross-linked digested chromatin extracted from MCF7 cells diluted into calf serum.

A commercially available nucleosome preparation produced by digestion of chromatin extracted from MCF7 cells in which the DNA and proteins in the nucleosome are cross-linked for stability (ensuring that all histones present in the preparation are incorporated into intact nucleosomes) was assayed using an ELISA method for the nucleosome associated histone variant macroH2A2 using a solid phase anti-histone capture antibody that binds intact nucleosomes and a biotinylated affinity purified polyclonal anti-histone variant macroH2A2 detection antibody. The nucleosome sample was serially diluted in fetal calf serum and was tested in duplicate in the ELISA. Neat fetal calf serum was also run in the ELISA as a control sample containing no cell free nucleosomes. The assay method was as follows: A solution of anti-histone antibody in 0.1M phosphate buffer pH 7.4 was added to microtitre wells (100 μL/well) and incubated overnight at 4° C. to coat the wells with capture antibody. Excess anti-histone antibody was decanted. A solution of bovine serum albumin (20 g/L) was added to the wells (200 μL/well) and incubated 30 minutes at room temperature to block excess protein binding sites on the wells. Excess bovine serum albumin solution was decanted and the wells were washed three times with wash buffer (200 μL/well, 0.05M TRIS/HCl buffer pH 7.5 containing 1% Tween 20). Sample (10 μL/well) and assay buffer (50 μL/well, 0.05M TRIS/HCl pH 7.5 containing 0.9% NaCl, 0.05% sodium deoxycholate and 1% Nonidet P40 substitute) were added to the wells and incubated overnight at 4° C. The sample and assay buffer mixture was decanted and the wells were washed three times with wash buffer (200 μL/well). A solution of biotinylated affinity purified polyclonal anti-histone variant macroH2A1.1 detection antibody was added (50 μL/well) and incubated 90 minutes at room temperature with mild agitation. Excess detection antibody was decanted and the wells were again washed three times with wash buffer (200 μL/well). A solution containing a streptavidin-horse radish peroxidase conjugate was added (50 μL/well) and incubated 30 minutes at room temperature with mild agitation. Excess conjugate was decanted and the wells were again washed three times with wash buffer (200 μL/well). A coloured substrate solution (100 μL/well, 2,2'-Azinobis [3-ethylbenzothiazoline-6-sulfonic acid]-diammonium salt) was added and incubated 20 minutes at room temperature with mild agitation. The optical density (OD) of the wells was measured at a wavelength of 405 nm using a standard microtitre plate reader. A dose response curve of increasing colour with increasing nucleosome associated histone variant macroH2A2 concentration was observed with a low background signal observed in the absence of histone variant macroH2A2 (fetal calf serum). The positive ELISA signal indicates that the histone variant macroH2A2 detected by the ELISA is incorporated within a nucleosome as (i) no free histones are present in the sample and (ii) the capture antibody used binds to histones within intact nucleosomes and does not bind to histone H2. The results are shown in FIG. 2.

EXAMPLE 3

Figure 3:
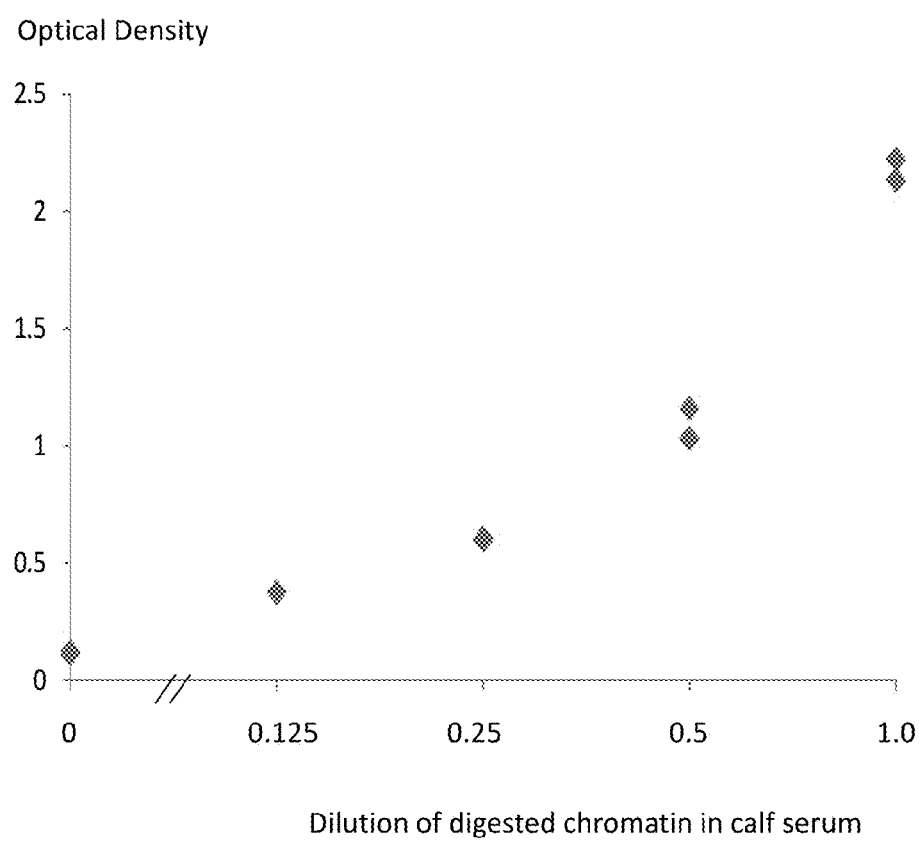
FIG. 3. ELISA dose response curve for the detection of histone variant H2AZ in cell free nucleosomes in cross-linked digested chromatin extracted from MCF7 cells diluted into calf serum.

A commercially available nucleosome preparation produced by digestion of chromatin extracted from MCF7 cells in which the DNA and proteins were cross-linked for stability (ensuring all histones present are incorporated into intact nucleosomes) was tested using an ELISA method for nucleosome associated histone variant H2AZ using a solid phase anti-histone capture antibody that binds intact nucleosomes and does not bind histone H2 and a biotinylated affinity purified polyclonal anti-histone variant H2AZ detection antibody. The details of the assay procedure are similar to those described in EXAMPLE 2 above. A reproducible dose response curve of increasing colour with increasing nucleosome associated histone variant H2AZ concentration was observed with a low background signal observed in the absence of nucleosome associated histone variant H2AZ (fetal calf serum). The positive ELISA signal indicates that the histone variant macroH2A2 detected is incorporated within a nucleosome as (i) no free histones are present in the sample and (ii) the capture antibody used binds to histones within intact nucleosomes and does not bind to histone H2. The results are shown in FIG. 3.

EXAMPLE 4

We used two nucleosome ELISA methods of the current art to measure the circulating cell free nucleosome content of serum and plasma blood samples taken from 20 healthy subjects. The first current ELISA method (ELISA 1) was the Roche Cell Death ELISA and the other (ELISA 2) an ELISA employing an anti-histone capture antibody and an anti-histone-DNA complex detection antibody. The nucleosome levels detected by both current nucleosome ELISA methods were both lower in normal plasma than in normal serum. The normal range (expressed in optical density units) for the serum level of nucleosomes was calculated (mean±2 standard deviations of the mean of the 20 healthy subject serum results) to be 0-4.3 OD units for ELISA 1 and 0-1.4 for ELISA 2. The respective ranges for plasma were 0-0.95 and 0-0.96. The results are shown in FIG. 4.

We also measured the levels of nucleosomes containing a histone PTM and two nucleotides as well as the three nucleosome associated histone variants mH2A1.1, mH2A2 and H2AZ, in the same samples. The results show that the serum samples taken from healthy subjects have uniformly low levels of nucleosomes containing histone variants or PTM or nucleotides. The normal ranges (expressed as optical density) for the serum level of nucleosomes containing histone variants, PTM or nucleotides were; (a) 0-0.36 for mH2A1.1, (b) 0.05-0.78 for mH2A2, (c) 0.11-0.58 for H2AZ, (d) 0.06-0.61 for P-H2AX (Ser139), (e) 0.06-0.36 for 5-methylcytosine and (f) 0.03-0.36 for 5-hydroxymethylcytrosine. The measured EDTA plasma results were higher for all 20 healthy subjects. The results are shown in FIGS. 5, 6, 7, 8, 9 and 10.

EXAMPLE 5

We measured cell free nucleosomes in EDTA plasma taken from 13 healthy subjects and 55 subjects with cancer of the stomach, large intestine, rectum, lung (small cell carcinoma and various non-small cell carcinomas), breast, ovary, prostate, kidney and various oral cancers (oral cavity, palate, pharynx and larynx). All of the samples from healthy subjects and cancer patients were positive for cell free nucleosomes. However, the levels detected in samples taken from cancer subjects were higher than found in samples from healthy subjects and the results showed that healthy and cancer subjects can be discriminated. For example the normal range calculated in OD terms as the mean±2 standard deviations in the mean, for the H2AZ nucleosome assay was 0-0.95. Using this cut-off level of 0.95; all 13 healthy subjects were negative for elevated nucleosome H2AZ levels. By contrast a positive result for elevated nucleosome H2AZ levels was found for 46 of the 55 cancer samples (an overall clinical sensitivity of 84%) including 100% (8 of 8) of stomach 100% (5 of 5) of large intestinal, 67% (2 of 3) of rectal, 83% (5 of 6) of small cell lung, 79% of non-small cell lung, 50% (3 of 6) of breast, 100% (1 of 1) of ovarian, 100% (1 of 1) of pancreas, 80% (4 of 5) of prostate, 100% (1 of 1) of kidney and 100% (5 of 5) of oral cancer samples. The results are shown in FIG. 19.

Similarly for the nucleosome associated mH2A1.1 assay the normal range was 0-0.91. Using this cut-off value all 13 healthy samples were negative and 64% (35 of 55) of cancer samples were positive. For the nucleosome associated P-H2AX(Ser139) assay the normal range was 0-1.08. Using this cut-off value all 13 healthy samples were negative and 60% (33 of 55) of cancer samples were positive. Nucleosome associated 5-methylcytosine was also measured and the assay the normal range was 0-1.41. Using this cut-off value all 13 healthy samples were negative and 55% (30 of 55) of cancer samples were positive.

We also used the methods of the invention to measure a variety of other nucleosome associated structures in the same samples. The results of these immunoassays were compiled to provide a profile of nucleosome structures in samples taken from cancer patients normalised relative to detected levels of nucleosomes containing 5-methylcytosine. We compared the resulting profiles to the nucleosome structure of samples taken from healthy subjects. The nucleosome structure profile of cell free nucleosomes was found to be different to those of healthy subjects. The results are shown in FIG. 23. We similarly compiled nucleosome structure profiles for samples taken from a variety of non-cancer diseases and compared these to the profile of nucleosomes in samples taken from cancer patients and from healthy subjects. The results are shown in FIG. 24.

Figure 20:
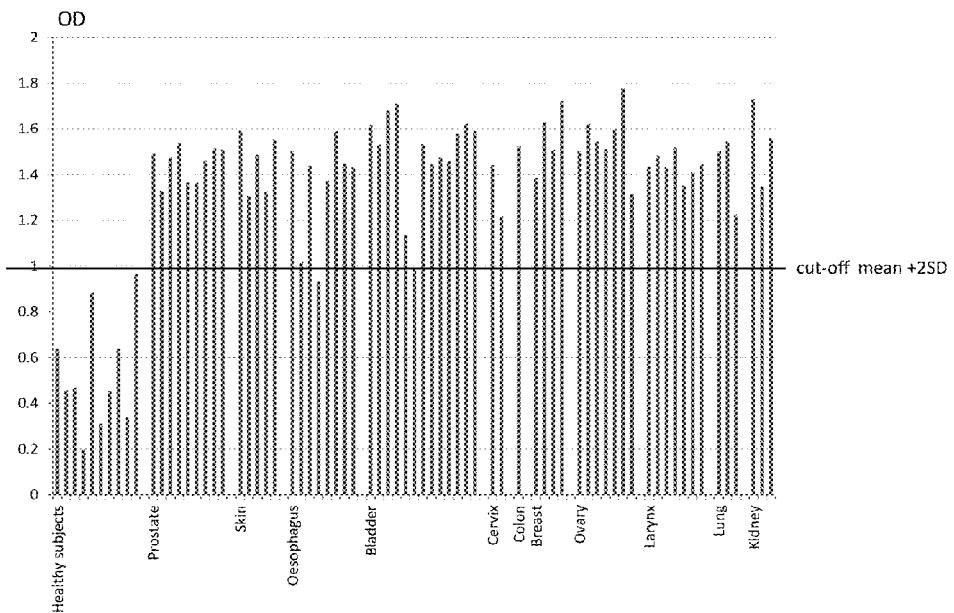
FIG. 20. Cell free nucleosome associated histone variant H2AZ levels detected for EDTA plasma samples taken from 10 healthy volunteers and 61 cancer patients. The cut-off point defined as the mean value of the healthy samples plus two standard deviations in the mean is shown.

We then performed another similar experiment including samples from 10 healthy subjects and a further 62 patients with cancer of various types. The results were similar to the first experiment. For example using the results for nucleosome associated histone variant H2AZ and a cut-off of mean+2 standard deviations of the mean of the results for healthy subjects, negative results were obtained for all 10 healthy subjects and positive results were obtained for 95% (59 of 62) of cancer patients including 9 of 9 prostate cancer patients, 5 of 5 skin cancer patients, 6 of 8 esophagus cancer patients, 12 of 13 bladder cancer patients, 2 of 2 cervix cancer patients and 1 of 1 colon cancer patients, 4 of 4 breast cancer patients, 7 of 7 ovary cancer patients, 7 of 7 larynx cancer patients, 3 of 3 lung cancer patients and 3 of 3 renal cancer patients. This result indicates that nucleosome associated histone variants are clinically sensitive biomarkers for cancer. The results are shown in FIG. 20.

EXAMPLE 6

We used two nucleosome ELISA methods of the current art to measure the circulating cell free nucleosome content of EDTA plasma samples taken from 3 subjects with colon cancer, 13 subjects with lung cancer, 2 subjects with pancreatic cancer, 1 subject with oral cancer and a nucleosome sample produced from healthy subjects according to method of Holdenrieder (*Holdenrieder et al, 2001). The first current ELISA method (ELISA 1) was the Roche Cell Death ELISA and the other (ELISA 2) an ELISA employing an anti-histone capture antibody and an anti-histone-DNA complex detection antibody.

We also measured the levels of nucleosomes containing three variant histones, a histone PTM and two nucleotides. The results show that, although low nucleosome results for ELISA methods of the current art were detected for most subjects, particularly for pancreatic and oral cancer patient, most of these samples have higher detectable levels of nucleosomes that contain one or more nucleosome associated variant histones. The results for samples taken from 3 subjects with colon cancer, 13 subjects with lung cancer, 2 subjects with pancreatic cancer and 1 subject with oral cancer are shown in FIGS. 11, 12, 13 and 14 respectively. Significant nucleosome associated histone variant levels were detected in 16 of the 19 cancer samples (all but 3 lung cancer samples). In addition nucleosome associated 5-hydroxymethylcytosine was detected in 12 of the 19 cancer samples and nucleosome associated 5-methylcytosine was detected in all 19 cancer samples.

Figure 15:
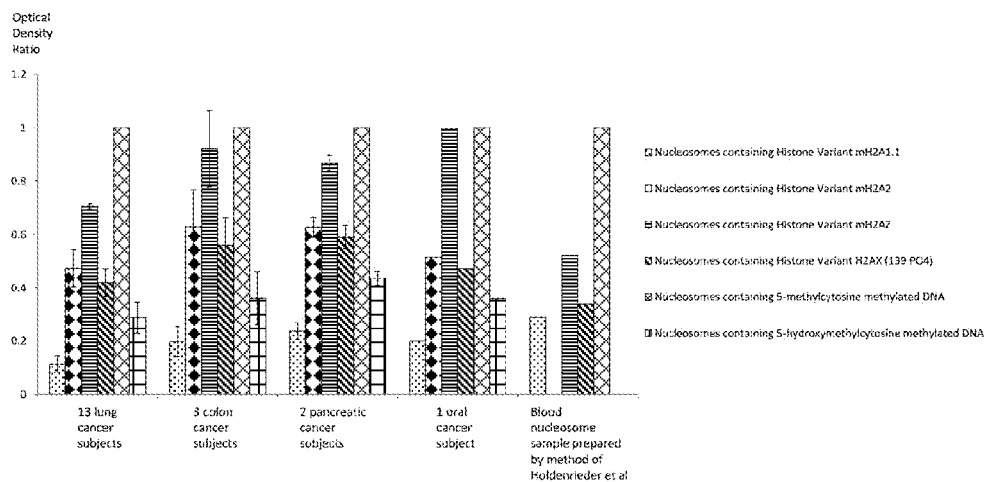
FIG. 15. Cell free nucleosome associated levels of types of histones and nucleotides detected for EDTA plasma samples taken from 4 different cancer diseases normalised as a proportion of nucleosome associated 5-methylcytosine methylated DNA levels detected using ELISA methods of the invention. Normalised levels for a sample containing nucleosomes from healthy volunteers produced by the method of *Holdenrieder et al 2001 is shown for comparison.

Furthermore the pattern of nucleosome levels containing different histone variant levels is not uniform for all subjects but displays different patterns for different cancers tested. To facilitate comparison between results for subjects with the same or different cancers; the results for the nucleosome tests (for nucleosomes containing macroH2A1.1, macroH2A2, H2AZ, P-H2AX(Ser139), 5-methylcytosine and 5-hydroxymethylcytosine) were normalised as a proportion of the OD signal observed for nucleosomes containing 5-methylcytosine. The normalised results (with error bars showing the standard deviation in results where samples from more than one subject were tested) are shown for each cancer in FIG. 15 as well as the same results for the nucleosome sample produced from healthy subjects (mH2A2 and 5-hydroxymethylcytosine were not measured for this sample). FIG. 15 shows that the distribution pattern of nucleosomes containing the different normalised histone variants, nucleotides or PTM in all four cancers investigated differs quite markedly to the distribution of nucleosomes in the sample from healthy subjects. Thus the present invention can be used as a method for the detection of cancer in a simple blood based screening test. It will be clear to those skilled in the art that the invention includes the testing of nucleosomes containing other further histone variants, nucleotides and/or histone modifications to further or better discriminate between circulating cell free nucleosomes of tumour or other disease origin.

Furthermore the pattern of nucleosome types observed differs for different cancer types. For example; the sample taken from a subject with oral cancer has lower normalised levels of both nucleosomes containing mH2A2 or P-H2AX (Ser139) than any of the other three cancer types. Similarly, samples from subjects with pancreatic cancer can be distinguished from samples from subjects with colon cancer on the basis of a different normalised level of nucleosomes containing variant macroH2A1.1. Thus the present invention can be used as a method to diagnose cancer generally and to distinguish a particular cancer type. It will be clear to those skilled in the art that the invention includes the testing of nucleosomes containing other further histone variants and/or histone modifications and/or nucleotides to further or better discriminate between circulating cell free nucleosomes of different specific tumour origin or other disease origin.

EXAMPLE 7

Figure 21:
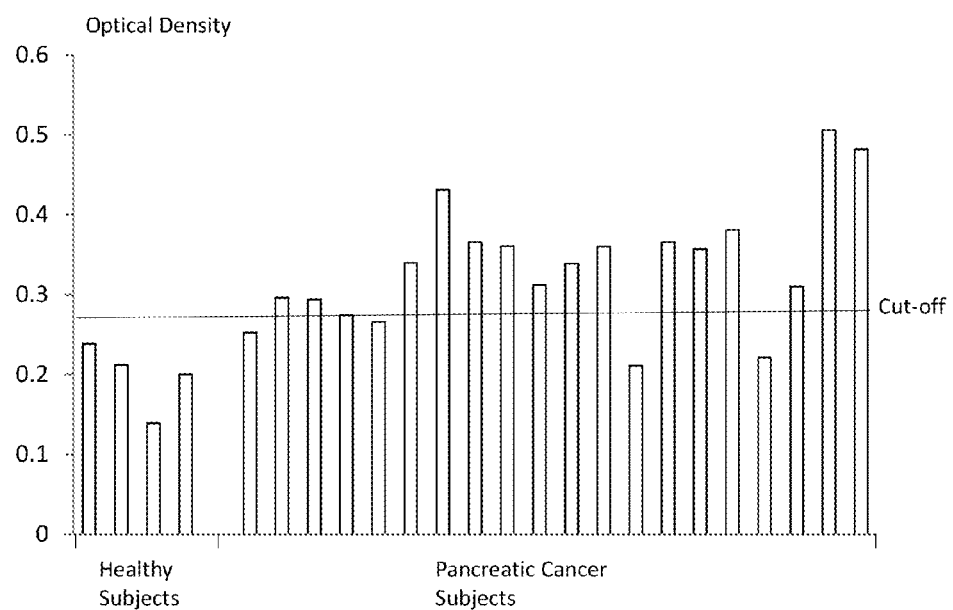
FIG. 21. Cell free nucleosome associated histone variant H2AZ levels detected for serum samples taken from 4 healthy volunteers and 20 pancreatic cancer patients. The cut-off point shown is defined as the mean value of the healthy samples plus two standard deviations in the mean.

We measured the nucleosome associated histone variant levels in serum samples taken from 4 healthy subjects and 20 serum samples taken from subjects with pancreatic cancer using the method of the invention as described above. Using a cut-off level of 0.27 (mean+2 standard deviations of the levels found in healthy patients), the nucleosome associated H2AZ levels were elevated in 80% (16 of 20) of the samples taken from pancreatic cancer patients and none of the healthy subjects. The results are shown in FIG. 21.

EXAMPLE 8

We measured the nucleosome associated histone H2AZ levels of some human samples taken from cancer patients using a biotinylated anti-H2AZ detection antibody as described in Example 3. The method was performed twice using two different monoclonal clonal anti-histone capture antibodies to determine if the H2AZ results were repeatable for different capture antibodies. The results in FIG. 16 show that the nucleosome associated histone H2AZ levels of the two assays are linearly related with a line of best fit that intercepts at approximately zero. The units are simple optical density readings.

EXAMPLE 9

Figure 22:
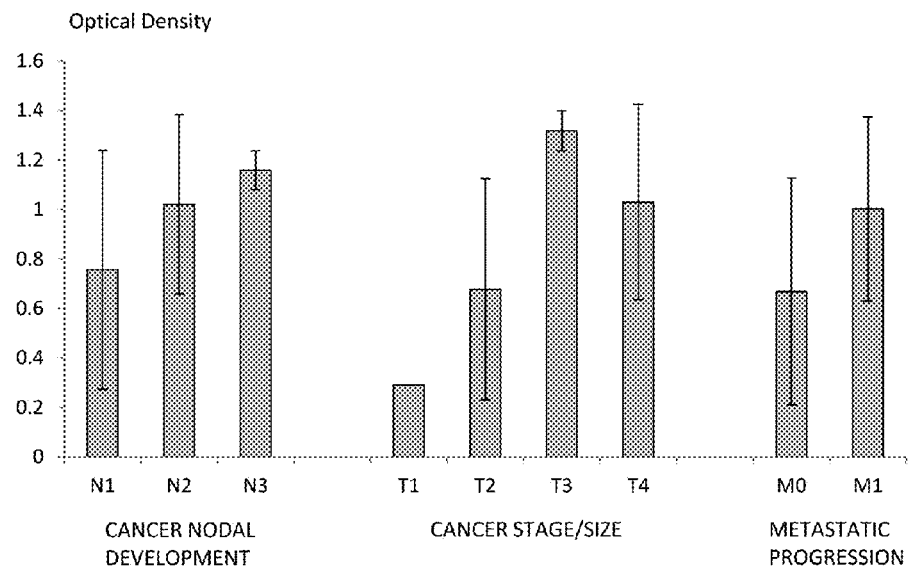
FIG. 22. Cell free nucleosome associated histone variant H2AZ levels detected for EDTA plasma samples taken from lung cancer patients with increasing tumour size, stage and nodal development of disease.

We measured the nucleosome associated histone H2AZ levels of human EDTA plasma samples taken from lung cancer patients as described in Example 3. The levels detected were correlated with the disease progression of the patients. The results shown in FIG. 22 indicate that nucleosome associated histone H2AZ levels increase with severity of disease in terms of size, stage, nodal spread and distant metastatic spread and nucleosome associated histone H2AZ levels may be used, alone or as part of a diagnostic panel, as indicators of disease nodal, size, stage or metastatic progression,

REFERENCES

Allen et al, A simple method for estimating global DNA methylation using bisulfite PCR of repetitive DNA elements. Nucleic Acids Research: 32(3) e38DOI: 10.1093/nar/gnh032

Bawden et al, Detection of histone modification in cell-free nucleosomes. WO 2005/019826, 2005

Boulard et al, Histone variant macroH2A1 deletion in mice causes female-specific steatosis. Epigenetics & Chromatin: 3(8), 1-13, 2010 Cell Biolabs, Inc. Product Manual for "Global DNA Methylation ELISA Kit (5'-methyl-2'-deoxycytidine Quantitation", 2011

Dai et al, Detection of Post-translational Modifications on Native Intact Nucleosomes by ELISA. http://www.jove.com/details.php?id=2593 doi: 10.3791/2593. J Vis Exp. 50 (2011).

Deligezer et al, Sequence-Specific Histone Methylation Is Detectable on Circulating Nucleosomes in Plasma. Clinical Chemistry 54(7), 1125-1131, 2008

Epigentek Group Inc, Methylamp™ Global DNA Methylation Quantification Kit, User Guide, Version 2.0802, 2009

Esteller, Cancer epigenomics: DNA methylomes and histone-modification maps Nature Reviews Genetics: 8, 286-298, 2007

Feinberg and Vogelstein, Hypomethylation distinguishes genes of some human cancers from their normal counterparts. Nature: 301, 89-92, 1983

Grutzmann et al, Sensitive Detection of Colorectal Cancer in Peripheral Blood by Septin 9 DNA Methylation Assay. PLoS ONE 3(11): e3759. doi:10.1371/journal.pone.0003759, 2008

Hervouet et al, Disruption of Dnmt1/PCNA/UHRF1 Interactions Promotes Tumorigenesis from Human and Mice Glial Cells PLoS ONE 5(6): e11333. doi:10.1371/journal.pone.0011333, 2010

Hua et al, Genomic analysis of estrogen cascade reveals histone variant H2A.Z associated with breast cancer progression. Molecular Systems Biology 4; Article number 188; doi:10.1038/msb.2008.25, 2008

Herranz and Esteller, DNA methylation and histone modifications in patients with cancer: potential prognostic and therapeutic targets. Methods Mol Biol. 361:25-62, 2007

Holdenrieder et al, Nucleosomes in serum of patients with benign and malignant diseases. Int. J. Cancer (Pred. Oncol.): 95, 114-120, 2001

*Holdenrieder et al, Nucleosomes in Serum as a Marker for Cell Death. Clin Chem Lab Med; 39(7), 596-605, 2001

Holdenrieder et al, Cell-Free DNA in Serum and Plasma: Comparison of ELISA and Quantitative PCR. Clinical Chemistry: 51(8), 1544-1546, 2005

Holdenrieder and Stieber, Clinical use of circulating nucleosomes. Critical Reviews in Clinical Laboratory Sciences; 46(1): 1-24, 2009

Kapoor et al, The histone variant macroH2A suppresses melanoma progression through regulation of CDK8. Nature: 468, 1105-1111, 2010

Mansour et al, The Prognostic Significance of Whole Blood Global and Specific DNA Methylation Levels in Gastric Adenocarcinoma. PLoS ONE 5(12): e15585. doi: 10.1371/journal.pone.0015585, 2010

Moore et Genomic DNA hypomethylation as a biomarker for bladder cancer susceptibility in the Spanish Bladder Cancer Study: a case—control study. The Lancet Oncology: 9(4), 359-366, 2008

Ogoshi et al, Genome-wide profiling of DNA methylation in human cancer cells. Genomics: In Press, 2011

Pennings et al, DNA methylation, nucleosome formation and positioning. Briefings in functional genomics and proteomics: 3(4), 351-361, 2005

Rodriguez-Paredes and Esteller, Cancer epigenetics reaches mainstream oncology. Nature Medicine: 17(3), 330-339, 2011

Salgame et al, An ELISA for detection of apoptosis. Nucleic Acids Research, 25(3), 680-681, 1997

Sporn et al, Histone macroH2A isoforms predict the risk of lung cancer recurrence. Oncogene: 28(38), 3423-8, 2009

Stroud et al, 5-Hydroxymethylcytosine is associated with enhancers and gene bodies in human embryonic stem cells. Genome Biology: 12:R54, 2011

Tachiwana et al, Structures of human nucleosomes containing major histone H3 variants. Acta Cryst: D67, 578-583, 2011

Ting Hsiung et al, Global DNA Methylation Level in Whole Blood as a Biomarker in Head and Neck Squamous Cell Carcinoma. Cancer Epidemiology, Biomarkers & Prevention: 16(1), 108-114, 2007 van Nieuwenhuijze et al, Time between onset of apoptosis and release of nucleosomes from apoptotic cells: putative implications for sysytemic lupus erythematosus. Ann Rheum Dis; 62: 10-14, 2003

Vasser et al, Measurement of Global DNA Methylation. Genetic Engineering and Biotechnology News: 29(7), 2009

Whittle et al, The Genomic Distribution and Function of Histone Variant HTZ-1 during *C. elegans* Embryogenesis. PLoS Genet 4(9): 1-17, 2008

Zee et al, Global turnover of histone post-translational modifications and variants in human cells Epigenetics & Chromatin. 3(22): 1-11, 2010

Zhang et al, Analysis of global DNA methylation by hydrophilic interaction ultra high-pressure liquid chromatography tandem mass spectrometry. Analytical Biochemistry: 413(2), 164-170, 2011

The invention claimed is:

1. A method of treating cancer, comprising:
   (a) obtaining a body fluid sample from a patient;
   (b) detecting a level of cell free nucleosome comprising a histone variant or histone isoform in the body fluid sample, comprising the steps of:
      (i) contacting the body fluid sample with a first binding agent which binds to (1) nucleosomes or (2) the histone variant or histone isoform;
      (ii) contacting the sample bound in step (i) with a second binding agent which binds to (1) the histone variant or histone isoform when the first binding agent binds to nucleosomes, or (2) nucleosomes when the first binding agent binds to the histone variant or histone isoform; and
      (iii) detecting or quantifying the binding of said second binding agent in the body fluid sample;
   (c) identifying the patient as suffering from the cancer based on the level of cell free nucleosome comprising a histone variant or histone isoform detected; and
   (d) administering a treatment to the patient identified as suffering from the cancer.

2. The method as defined in claim 1, wherein the cell free nucleosome is a mononucleosome or an oligonucleosome.

3. The method as defined in claim 1, wherein the body fluid sample is a blood, serum or plasma sample.

4. The method as defined in claim 1, wherein the cancer is a cancer of the bladder, breast, colon, cervix, esophagus, kidney, large intestine, lung, oral cavity, ovary, pancreas, prostate, rectum, skin or stomach.

5. The method as defined in claim 4, wherein the cancer is a cancer of the colon, lung, oral cavity or pancreas.

6. The method of claim 1, wherein the step for detecting the level of cell free nucleosome containing a histone variant or histone isoform in the body fluid sample comprises the steps of:
   (i) contacting the body fluid sample with a first binding agent which binds to nucleosomes;
   (ii) contacting the sample bound in step (i) with a second binding agent which binds to the histone variant or histone isoform; and
   (iii) detecting or quantifying the binding of said second binding agent to the histone variant or histone isoform in the body fluid sample.

7. The method of claim 1, wherein the step for detecting the level of cell free nucleosome containing a histone variant or histone isoform in the body fluid sample which comprises the steps of:
   (i) contacting the body fluid sample with a first binding agent which binds to the histone variant or histone isoform;
   (ii) contacting the sample bound in step (i) with a second binding agent which binds to nucleosomes; and
   (iii) detecting or quantifying the binding of said second binding agent to nucleosomes in the body fluid sample.

8. The method as defined in claim 1, wherein the binding agent is an antibody.

9. The method according to claim 1, wherein the cell free nucleosome containing the histone variant or histone isoform is detected or measured as one of a panel of measurements.

* * * * *